US011822772B2

(12) United States Patent
Anderson et al.

(10) Patent No.: US 11,822,772 B2
(45) Date of Patent: Nov. 21, 2023

(54) DISPLAYING VISUALIZED TESTING RESULTS

(71) Applicant: CERNER INNOVATION, INC., Kansas City, KS (US)

(72) Inventors: Matt R. Anderson, Kansas City, MO (US); Jason Mitchell, Lees Summit, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 0 days.

(21) Appl. No.: 17/500,101

(22) Filed: Oct. 13, 2021

(65) Prior Publication Data

US 2023/0111517 A1 Apr. 13, 2023

(51) Int. Cl.
*G06F 3/0484* (2022.01)

(52) U.S. Cl.
CPC .. *G06F 3/0484* (2013.01); *G06F 2203/04806* (2013.01)

(58) Field of Classification Search
None
See application file for complete search history.

(56) References Cited

U.S. PATENT DOCUMENTS

| | | | |
|---|---|---|---|
| 8,527,909 B1* | 9/2013 | Mullany | G06F 3/04883 345/173 |
| 2006/0265249 A1* | 11/2006 | Follis | G16H 10/60 715/254 |
| 2009/0113295 A1* | 4/2009 | Halpern | A61B 5/14532 715/273 |
| 2011/0246882 A1* | 10/2011 | Kollenkark | G06F 16/447 715/716 |
| 2014/0304005 A1* | 10/2014 | Hughes | G06F 3/041 705/2 |
| 2017/0185744 A1* | 6/2017 | Okabe | G16H 20/10 |
| 2019/0378216 A1* | 12/2019 | Fiete | G06Q 40/08 |

OTHER PUBLICATIONS

NickJr et al. ("Plot data points beyond the axis maximum as the maximum", Stack Overflow) (Year: 2013).*

* cited by examiner

*Primary Examiner* — William L Bashore
*Assistant Examiner* — Gabriel Mercado
(74) *Attorney, Agent, or Firm* — KRAGULJAC LAW GROUP, LLC

(57) ABSTRACT

Disclosed are various methods of presenting result visualizations for test results. The visualization may include a timeline, a test label area, a test parameter indicator, and a test value representation. The test label area includes a test label associated with the test. The test parameter indicator is associated with the test provided at a location corresponding with the test label of the test label area and with a location corresponding to a test time of the timeline, including a first test parameter indicator end associated with the upper test parameter threshold and a second test parameter indicator end associated with a lower test parameter threshold. The test value representation of a test value extends away from the test parameter indicator and proportionally represents the test value relative to an upper test limit and the test value to a lower test limit.

20 Claims, 13 Drawing Sheets

DISPLAYING VISUALIZED TESTING RESULTS

BACKGROUND

Various professionals and other users often quickly review numerous test results as taken over an extended period of time. Existing systems for displaying test results require the user to process and analyze presented context, which may lead to errors or delays or provide a minimal amount of information for a given screen size, which may reduce efficiency.

SUMMARY

At a high level, aspects described herein relate to a result visualization system that generates an easy and quick reference for various test results. This is particularly beneficial when used on smaller screens, such as a smart phone or a smart watch. Further, the technology allows context to be maintained regardless of the scale at which the results are being viewed.

A graphical user interface (GUI) of embodiments includes a timeline, a test label area, a test parameter indicator, and a test value representation. The timeline extends in a first direction of the GUI. The test label area includes a test label associated with a test, the test label area extending in a second direction of the GUI, the second direction being perpendicular to the first direction. The test is associated with an upper test parameter threshold and a lower test parameter threshold, and the test is associated with a test result comprising a test value. The test parameter indicator is associated with the test provided at a location corresponding with the test label of the test label area and with a location corresponding to a test time of the timeline. The test parameter indicator extends in the second direction of the GUI from a first test parameter indicator end associated with the upper test parameter threshold to a second test parameter indicator end associated with a lower test parameter threshold. The test value representation of the test value extends away from the test parameter indicator in the first direction of the GUI. The test value representation intersects the test parameter indicator at or between the first test parameter indicator end and the second test parameter indicator end. The intersection location proportionally represents the test value relative to the upper test parameter threshold and the test value to the lower test parameter threshold.

A computerized method may include receiving a test result comprising a test value, the test result being associated with a test, and rendering a graphical user interface as described herein to provide a visualization of the test value.

This summary is intended to introduce a selection of concepts in a simplified form that is further described in the detailed description section of the present disclosure. The summary is not intended to identify key or essential features of the claimed subject matter, nor is it intended to be an aid in determining the scope of the claimed subject matter. Additional objects, advantages, and novel features of the technology will be set forth in part in the description that follows, and in part will become apparent to those skilled in the art upon examination of the disclosure or learned through practice of the technology.

BRIEF DESCRIPTION OF THE DRAWINGS

The present technology is described in detail below with reference to the attached drawing figures, in which:

FIG. 4A illustrates an example prior art visualization graphical user interface displaying on a client computing device;

FIG. 4B illustrates an example result visualization graphical user interface displaying on a client computing device, in accordance with an aspect described herein;

DETAILED DESCRIPTION

Figure 1:
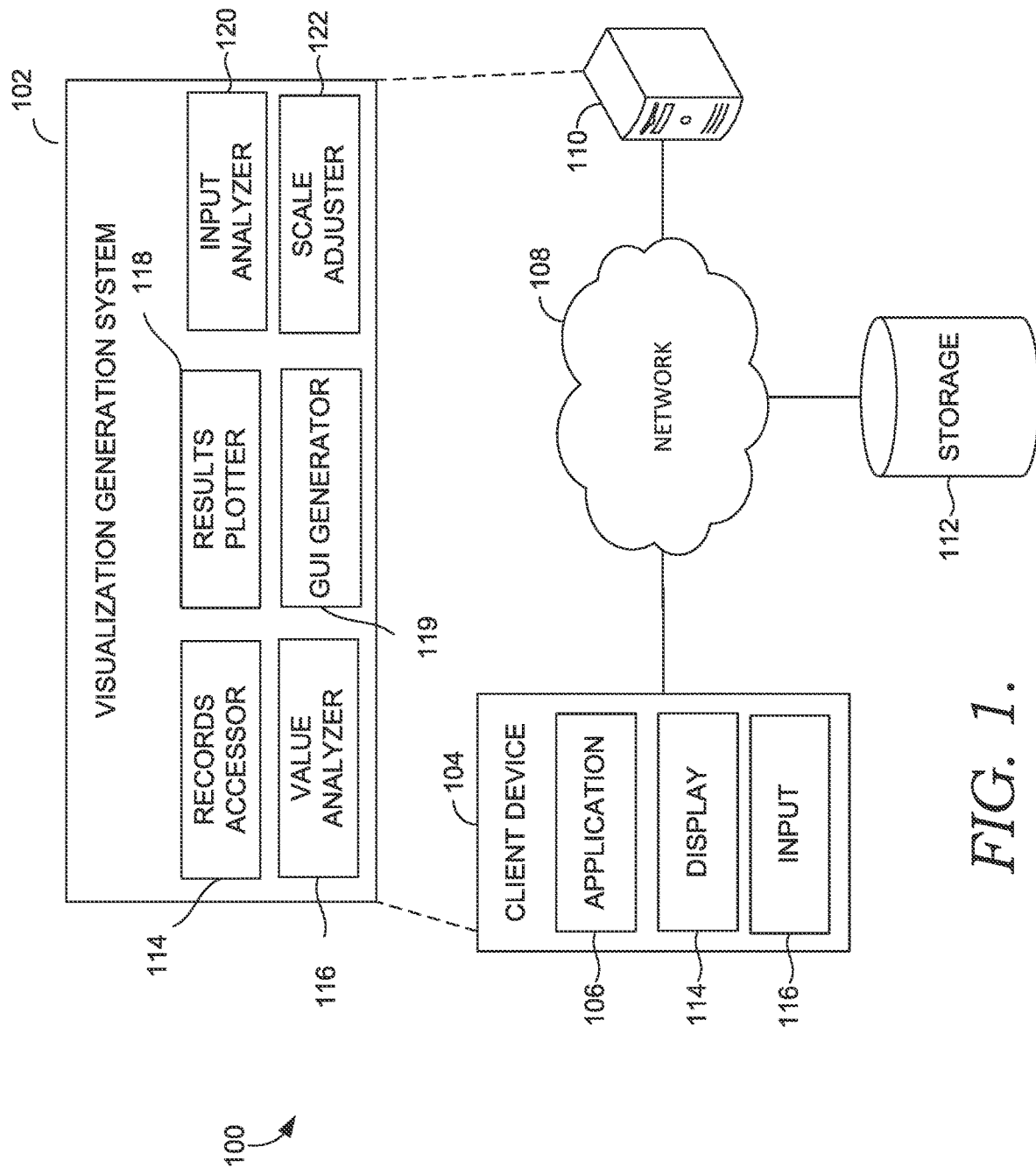
FIG. 1 is an example operating environment in which an example visualization generation system is employed, in accordance with an aspect described herein.

Embodiments of the present disclosure provide easy and quick visualization of various test results. The test results are analyzed and displayed on a graphical user interface in such a manner that the user can quickly review the results, as well as how the results have changed over time, which tests were performed when, and other considerations. The user may also customize the view provided to different scales. As such, the user can determine which information to view across which timelines by providing a simple user input. The visualization may align to a timeline to give more clear information on when the test was administered. The visualization may also provide context with regard to the meaning of the results and how the results change over time.

An example field of use for some embodiments of the present disclosure is in the field of medicine. In this field, numerous medical and health tests may be given to a patient over an extended period of time. The contextual presentation of the test results allows for a medical professional to quickly and easily be able to analyze the test results, observe how the test results have changed over time, and determine which (if any) additional tests should be performed. The visualization also allows for the display on smaller screens than traditional computer screens, allowing the medical professional to use a smart phone, smart watch, or other computing device with a small screen.

Conventional methods of displaying test results usually include a columnar display that shows results with just a numerical value. The columnar display includes little to no analysis helping the user interpret the results. The columnar display also only allows a limited amount of information to be shown on a given screen size. The dates/times between adjacent columns may be long or short, with no visual indication provided to the user (other than the written dates/times themselves). For example, from a first column to a second column may be a difference of a day, while the second column to a third column may be a difference of a year. As such, reviewing test results on such columnar displays includes several disadvantages. First, the user must be able to see a numerical value as a test result and know how to interpret that test result. This may lead to the user not noticing important results. Second, the user is required to scroll through numerous columns to find the needed information and often cannot get a complete view of the test results in a single view. Third, the context of time spans between the columns may be missed, which can lead to an inaccurate interpretation of the results. Fourth, since the columnar displays are space inefficient, they typically must be viewed on large screens, such as on a stationary computer.

Embodiments of the present disclosure solve the described inadequacies by providing a graphical plot of test results with a summary label indicative of the timeframe and the results of the test. The user can thus get an idea of the timeframe and results in an easily viewable representation. This reduces the need for the user to understand the numerical value of a test result, because a representation interpreting the result is presented to the user. This also allows for easy context to be viewed as to when the tests were performed, timespans between the tests, when tests were given relative to other tests, and other timespan information that is lost in traditional columnar displays. The summary label may be provided with or without a numerical representation of a test value, based upon the scale of the display or other adjacent results. This information can be presented in smaller devices, allowing for a quick and easy reference to the test results. The smaller devices allow the user to review results quickly and easily, such as on a smart phone or a smart watch, without needing to be at a stationary computer.

As an example, and as will be further described, some embodiments of the present disclosure provide for a summary label that has a test parameter indicator that gives a visualization of the scale for the results of the test. The summary label can also include a test value representation that extends from a point on the test parameter indicator, thus providing a way to easily understand the results of the test by visually identifying where the test results fall relative to upper and lower test parameter thresholds. In this way, the timeline can represent many different types of tests, and a user can quickly visualize the different test results, even if each test result is on numerically different scales.

For instance, a hemoglobin A1C test has a lower test parameter threshold of 3.6% and an upper test parameter threshold of 5.6%, while a test for sodium level has a lower test parameter threshold of 135 mEq/L and an upper test parameter threshold of 145 mEq/L. Obviously, these examples not only have numerically different upper and lower thresholds, but also have different units. In embodiments of the technology that will be described, an A1C test and a sodium test can each be represented by a test parameter indicator that is positioned on the timeline to identify when the test was performed. Further, each test may include a test value representation that indicates the results of the test relative to where the test value representation intersects the test parameter indicator.

By using summary labels in this manner, many different tests can be represented in two-dimensions, such as a timeline extending in one direction and the test labels extending in the other direction. The way in which the test parameter indicator and the test value representation illustrates the results allows the results to be presented graphically without their units or even the value of the test itself, yet still conveys the same amount of information in a small area. Further, the test parameter indicator can extend in one direction on the timeline, while the test value representation intersects and extends perpendicularly away from the test parameter indicator. This arrangement allows the data to be compressed into a small area without losing information or context of the data.

Conventional methods that use charts or other display features can only be compressed to a certain point before the size of the entire chart must be reduced to provide the data in the small area. When this happens, it is not possible for many people to view the data on a smaller screen without manipulating the screen (scrolling across the chart or zooming in an out of certain parts of the chart). This limits the use of many conventional methods to places such as nursing stations or larger workstations. The advantages, however, that the current technology has over these conventional methods is that the method of display allows for greater compression, while still maintaining the contextual information. Thus, a physician can view the same information on a single watch face or phone screen, whereas previously, the physician would have had to manipulate the smaller screen to view the information or use a larger workstation.

Having described an example aspect, further description is provided with reference to the drawings. Turning first to FIG. 1, the figure illustrates a block diagram of example operating environment 100 suitable for use in implementing the described technology. As illustrated, the operating environment 100 is suitable for implementing a result visualization system 102.

It should be understood that the operating environment 100 shown in FIG. 1 is an example of one suitable operating environment. Among other components not shown, the operating environment 100 includes a client device 104 having application 106. The client device 104 communicates with a server 110 and a storage 112, via a network 108. The server 110 is shown implementing the result visualization system 102. In other embodiments, all, or a portion of the result visualization system 102, may be implemented on the client device 104.

With specific reference to FIG. 1 generally, it should be understood that this and other arrangements described herein are set forth only as examples. Other arrangements and elements (for example, machines, interfaces, functions, orders, and groupings of functions, etc.) can be used in addition to or instead of those shown, and some elements may be omitted altogether for the sake of clarity. It should also be understood that any number of client devices, servers, and other components may be employed within the operating environment 100, and such aspects are intended to be within the scope of the present disclosure. Each of the components in FIG. 1 may comprise a single device or multiple devices cooperating in a distributed environment or in the cloud.

Further, many of the elements described herein are functional entities that may be implemented as discrete or distributed components or in conjunction with other components, and in any suitable combination and location. Various functions described herein as being performed by one or more entities may be carried out by hardware, firmware, or software. For instance, some functions may be carried out by a processor executing instructions stored in memory, as will be further described with reference to FIG. 9.

Each of the components shown in FIG. 1, and within the figures generally, may be implemented via any type of computing device, such as one or more of computing device 900 described in connection to FIG. 9, for example. These components may communicate with each other via a network, such as the network 108, which may be wired, wireless, or both. The network 108 can include multiple networks, or a network of networks, but is shown in simple form so as not to obscure aspects of the present disclosure. By way of example, the network 108 can include one or more wide area networks (WANs), one or more local area networks (LANs), one or more public networks, such as the Internet, or one or more private networks. Where the network 108 includes a wireless telecommunications network, components such as a base station, a communications tower, or even access points (as well as other components) may provide wireless connectivity. Networking environments are commonplace in offices, enterprise-wide computer networks, intranets, and the Internet. Accordingly, network 108 is not described in significant detail.

Client devices, generally, such as the client device 104, can be any type of computing device capable of being operated by a user, which may be any person or entity that provides or utilizes aspects of the result visualization system 102. In some implementations, the client device 104 is the type of computing device described in relation to FIG. 9. For example, the client device 104 may be embodied as a personal computer (PC), a laptop computer, a mobile device, a smartphone, a tablet computer, a smart watch, a wearable computer, a personal digital assistant (PDA), a global positioning system (GPS) or device, a video player, a handheld communications device, a gaming device or system, an entertainment system, a vehicle computer system, an embedded system controller, a remote control, an appliance, a consumer electronic device, a workstation, any combination of these delineated devices, or any other suitable device. The client device 104 can include a display device for displaying a graphical user interface. A suitable example is provided by I/O port 918 of FIG. 9.

The client device 104 can include one or more processors and one or more computer-readable media. The computer-readable media may include computer-readable instructions executable by the one or more processors. The instructions may be embodied by one or more applications, such as the application 106, shown in FIG. 1. The application 106 is referred to as a single application for simplicity, but its functionality can be embodied by one or more applications in practice.

The application 106 is generally capable of facilitating the exchange of information between components of FIG. 1. For example, the application 106 can facilitate receiving information from a user and receiving or executing instructions provided by the visualization generation system 102. The application 106 may perform any or all of the steps of the visualization generation system 102. The application 106 may receive test result data or other information for display from visualization generation system 102, the server 110, the storage 112, or another source.

In some implementations, the application 106 comprises a web application, which can run in a web browser, and could be hosted at least partially on the server-side of the operating environment 100. The Application 106 may comprise a dedicated application, such as an application having analytics and display functionality. In some cases, the application 106 is integrated into the operating system (for example, as a service or program). It is contemplated that "application" be interpreted broadly. In some embodiments, the application 106 is integrated with the visualization generation system 102, which is illustrated as being executed by the server 110.

The server 110 generally supports aspects of the visualization generation system 102. The server 110 includes one or more processors and may comprise one or more computer-readable media. The computer-readable media includes computer-readable instructions executable by the one or more processors. The instructions may be executed by the one or more processors to implement one or more components of the visualization generation system 102. Though illustrated as distributed in nature, components of FIG. 1 can also be integrated in any fashion, including an aspect where the server 110 is integrated with the client device 104. The various method steps described herein may be performed by any combination of the client device 104, the server 110, or other computing devices. In some embodiments, the server 110 is part of an Electronic Health Record (EHR) system.

The storage 112 generally stores information including data, computer instructions (for example, software program instructions, routines, or services), or models used in embodiments of the described technologies. Although depicted as a database component, the storage 112 may be embodied as one or more data stores or may be in the cloud. In an aspect, the storage 112 may include electronic medical records stored as part of the EHR system.

As noted, the server 110 can execute one or more functions of the visualization generation system 102, which may include a records accessor 114, a value analyzer 116, a results plotter 118, a GUI generator 119, an input analyzer 120, and a scale adjuster 122. In other embodiments, one or more of the functions may be performed on the client device 104 or some other computing device. In one particular embodiment, the records accessor 114 may be performed by the server 110 while the other discussed functions may be performed at the client device 104.

In general, the records accessor 114 may access, pull, retrieve, review, or otherwise obtain data from one or more electronic health records or other data source. The records accessor 114 obtains a set of result data. The result data may be indicative of results of one or more tests, labs, readings, results, or other information. The result data may include numerical values for the one or more results. The result data may also include identifying information for a certain patient. The result data may include a timestamp for the one or more results, such that the results may be plotted according to the timestamps. The timestamp may be indicative of a date or time in which the test was taken, the result obtained, the sensor was read, etc.

In some embodiments, the results data may be retrieved from the storage 112, the client device 104, or a local sensor. The results data may be pulled from the EHR system, a set of current readings (for example, from a currently monitored sensor), a local record, or other repository of information.

The results data may include a mixture of current and previous readings, such that both may be displayed together for providing context.

The value analyzer 116 generally analyzes one or more of the results from the set of result data. The results may each be indicative of a single test result for a certain test. The certain test may have been provided to the patient at multiple times (for example, a first occurrence and a second occurrence). The certain test may have a label associated with the test values, such that the results may be tracked over time. The certain test may be identified by a standard nomenclature, such that it can be identified and uniformly compared. For example, if the same test was given by different medical professionals at different dates, the value analyzer 116 may still compare those results along a timeline.

The value analyzer 116 generally compares the one or more results to at least one threshold. In some embodiments, the value analyzer 116 compares a result against a set of thresholds to determine where the result falls amongst the thresholds. For example, the value analyzer 116 may compare the result against an upper test parameter threshold and a lower test parameter threshold. It will be understood by those of ordinary skill in the art that different test may have different high and low thresholds for upper and lower limit threshold values, and it will be understood what test values are considered, in-range high, in-range low, or critical. Based upon the comparison, the value analyzer 116 will determine if the result is above the upper test parameter threshold, below the lower test parameter threshold, or between the thresholds. As another example, the test result value relative to the thresholds may include a test value that is in-range high, out-of-range high, in-range low, out-of-range low, or a critical value. The value analyzer 116 may determine an appropriate label for value based upon the test value relative to the thresholds. The set of thresholds may include an upper test parameter threshold and a lower test parameter threshold. The upper test parameter threshold may be an upper threshold of a normal range for the certain test. The lower test parameter threshold may be a lower threshold of a normal range for the certain test.

In some embodiments, the thresholds are static and standardized. For a certain test, there may be an established set of thresholds to which the test value may be compared. The value analyzer 116 may access the set of thresholds for the certain test. In some other embodiments, the thresholds are variable. In these embodiments, the value analyzer 116 may determine or calculate a threshold or thresholds to be used. The threshold may be based, at least in part, on the specific user. For example, the threshold may be calculated or otherwise determined based upon one or more characteristics of the patent (such as age, weight, or medical history). In some embodiments, a user may be able to specify or adjust the thresholds such that the threshold may be customized to the particular patient by a medical professional.

The value analyzer 116 determines a summary label for one or more of the results. The summary label may include a test parameter indicator and a test value representation. The test parameter indicator provides a visual scale, and the test value representative provides a visual representation of the test value on the visual scale. Generally, the summary label provides a visual indication of the test value for the one or more results. The summary label provides an analysis of the test value relative to one or more thresholds by illustrating the test value representation proportionally with the test parameter indicator. For example, a summary label may provide a visual indication that the test value of the result is above or below a certain threshold. The summary label provides the indication at a glance even without a representation of the threshold value. The summary label may also provide an indication relative to the threshold without need for the numerical value of the result to be shown.

Figure 2A:
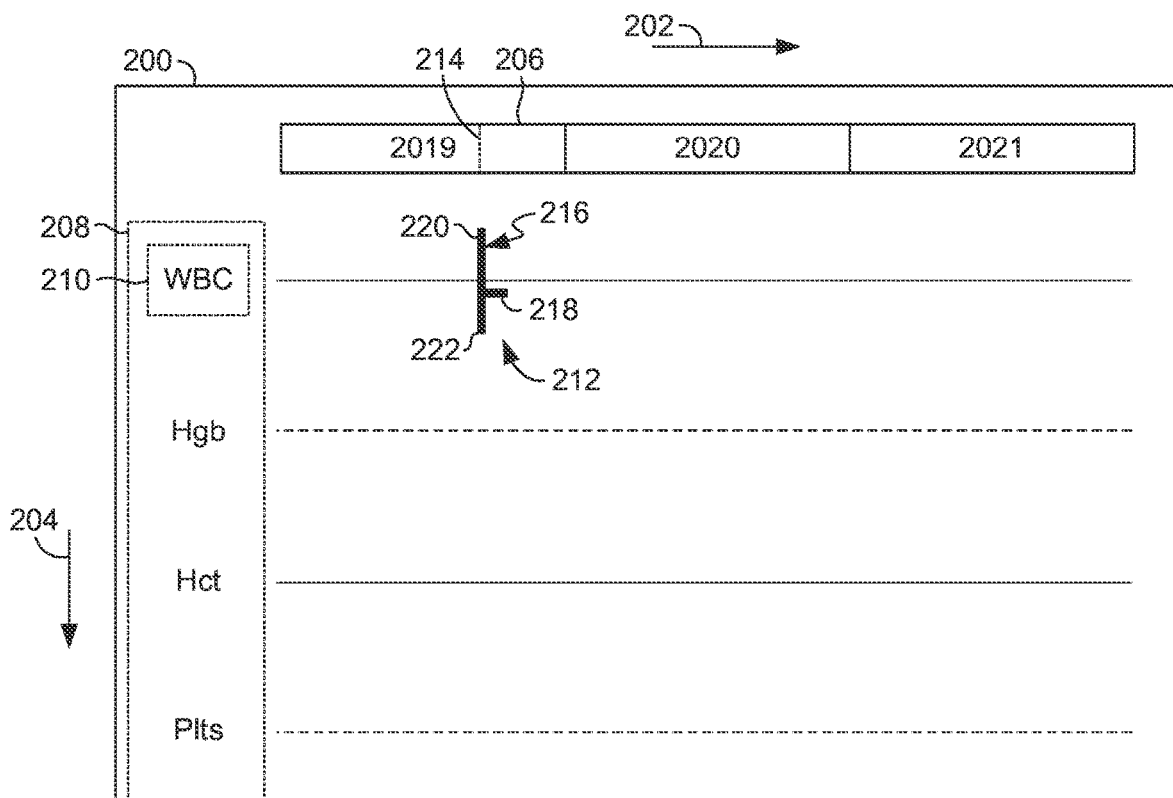
FIGS. 2A-2E are example summary labels for illustrating test results, in accordance with aspects described herein.

For example, FIG. 2A provides an example of a summary label 212. FIG. 2A illustrates a graphical user interface (also referred to as "GUI") 200. In this example, the graphical user interface 200 extends in a first direction 202 and a second direction 204. In some embodiments, the first direction 202 is perpendicular to the second direction 204. In the illustrated example, the first direction 202 extends horizontally relative to the second direction 204 that is illustrated as extending vertically. It will also be realized that first direction 202 and second direction 204 may extend across a graphical user interface in any direction. As shown, a timeline 206 extends in the first direction 202 and may include one or more date/time indications providing contextual information. Here, the timeline 206 is shown illustrating a length of time between 2019 and 2021. The graphical user interface 200 also comprises a test label area 208. In this example, the test label area 208 extends in the second direction 204. The test label area 208 may include one or more test labels, such as test label 210. These may indicate tests that may have been performed on the patient. The test label area 208 includes the test label 210 that corresponds to a specific test to which the summary label 212 is indicative of a test result thereof.

The summary label 212 is placed in a position relative to the timeline 206 and the test label area 208 such that context for the summary label 212 can be viewed by the user in the graphical user interface 200. The summary label 212 aligns with the test label 210 along the first direction 202 so as to provide an indication that the summary label 212 corresponds with the test label 210. The summary label 212 also aligns with a test time 214 along the second direction 204 so as to provide an indication of when the test was performed. The test time 214 is illustrated here using a dotted line, but it will be understood that in aspect of the present disclosure, the dotted line of the test time 214 is theoretical in nature and that the test time is indicated by the location summary label 212 relative to the timeline 206.

The summary label 212 in this example includes a test parameter indicator 216 and a test value representation 218. In an aspect, the test time 214 is indicated by the perpendicular alignment of the test parameter indicator 216 relative to the timeline 206. The test parameter indicator 216 extends from a first test parameter indicator end 220 to a second test parameter indicator end 222 in the second direction 204. In aspects, the first test parameter indicator end 220 is associated with an upper test parameter threshold, such as a top of a normal range for the certain test. The second test parameter indicator end 222 is associated with a lower test parameter threshold, such as a bottom of a normal range for the certain test. The test parameter indicator 216 provides an example scale from which the test value representation 218 extends in the first direction 202. The test value representation 218 provides a visual indication of the value of the test relative to the scale of the test parameter indication 216. Put another way, an intersection location is proportionally distributed at or between the first test parameter indicator end 220 and the second test parameter end 222 based on the test result of the test relative to the upper test parameter threshold and the lower test parameter threshold.

FIGS. 2B-2E show various embodiments of the summary labels. It will be understood that any of the summary labels illustrated can be provided on a graphical user interface, such as GUI 200 in manners provided by the present disclosure. However, for clarity and ease of discussing the technology, certain embodiments are individually illustrated. FIGS. 2B-2E show examples of summary label schemas that may be used to provide a visual representation of the analysis performed by the value analyzer 116. In the example schemas, example summary labels are shown in a way that provide visual information to the user in an easy-to-understand format in minimal space of the graphical user interface, and in manners that can be reduced in size, in any direction, while maintaining the context of information that the summary labels are intended to illustrate.

Figure 2B:
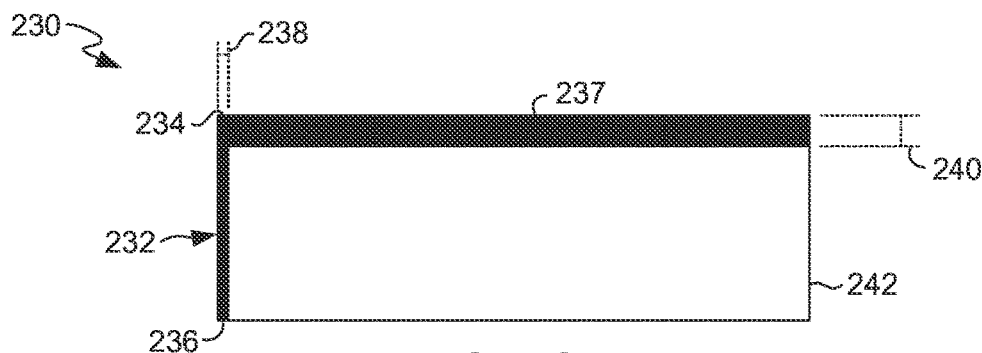

Accordingly, FIG. 2B provides a first summary label 230. In this example, the first summary label 230 comprises a first test parameter indicator 232. In an aspect of the present disclosure, the first summary label 230 may be used to indicate a test result that is greater than an upper test parameter threshold. The first test parameter indicator 232 comprises first test parameter indicator end 234 and a second test parameter end 236 of the first test parameter indicator 232. In this aspect, a test value representation 237 intersects the first test parameter indicator 232 at the first test parameter end 234 based on the test value exceeding the upper test parameter threshold. The test value representation 237 extends perpendicularly from the first test parameter indicator 232. In some aspects, the first summary label 230 may further comprise second test parameter indicator 242. In such aspects, the test value representation 237 can extend in direction towards the second test parameter indicator 242. The first test parameter indicator 232 may be parallel with the second test parameter indicator 242. In the illustration, the first test parameter indicator 232 comprises a first test parameter indicator width 238, which is illustrated by theoretical dashed lines, while the test value representation 237 comprises test value representation width 240, also illustrated using theoretical dashed lines. In some cases, to emphasize the test value exceeding the upper test parameter threshold, the test value representation width 240 is greater than the test parameter indicator width 238. In aspects where there is the second test parameter indicator 242, the first test parameter indicator width 238 or the test value representation width 240 may be larger than the second test parameter indicator width, which has not been illustrated for simplicity. In some cases, the test value can be positioned between the first test parameter indicator 232 and the second test parameter indicator 242. In some aspects, the test value can be positioned adjacent to the first test parameter indicator 232.

Figure 2C:
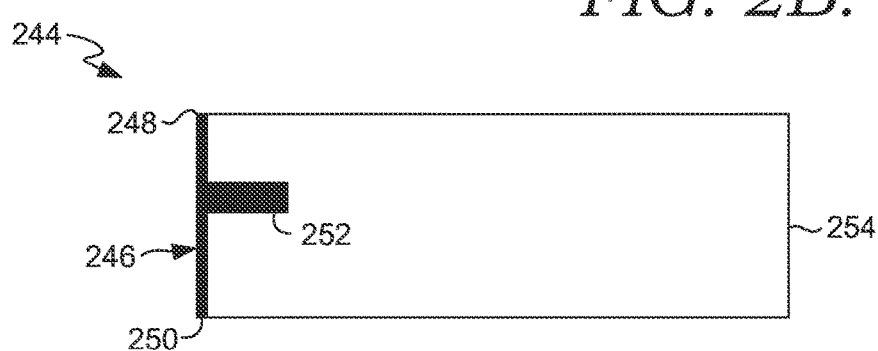

Referring to FIG. 2C, a second summary label 244 is provided. In this example, the second summary label 244 comprises first test parameter indicator 246. In an aspect of the present disclosure, the second summary label 244 may be used to indicate a test result that is between an upper test parameter threshold and a lower test parameter threshold. The first test parameter indicator 246 comprises first test parameter end 248 and a second test parameter end 250 of the first test parameter indicator 246. In this aspect, a test value representation 252 intersects the first test parameter indicator 246 between the first test parameter indicator end 248 and the second test parameter end 250 based on the test value being less than the upper test parameter threshold and greater than the lower test parameter threshold. As noted, a location of intersection between the test value representation 252 and the first test parameter indicator 246 can indicate a test value based on the location of intersection relative to the first test parameter end 248 and the second test parameter end 250. The test value representation 252 extends perpendicularly from the first test parameter indicator 246. In some aspects, the second summary label 244 may further comprise second test parameter indicator 254. In such aspects, the test value representation 252 can extend in a direction towards the second test parameter indicator 254. The first test parameter indicator 246 may be parallel with the second test parameter indicator 254. In aspects where there is the second test parameter indicator 254, the test value can be positioned between the first test parameter indicator 246 and the second test parameter indicator 254. In some aspects, the test value can be positioned adjacent to the first test parameter indicator 246.

Figure 2D:
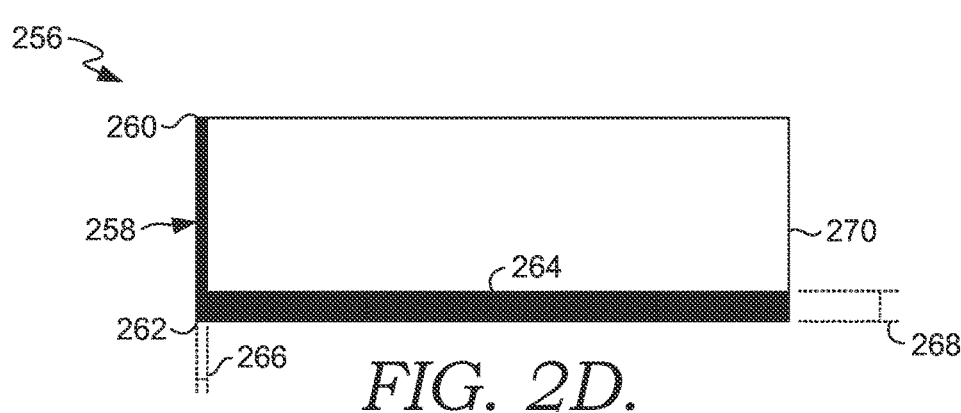

Referring now to FIG. 2D, a third summary label 256 is provided. In this example, the third summary label 256 comprises first test parameter indicator 258. In an aspect of the present disclosure, the first summary label 256 may be used to indicate a test result that is less than a lower test parameter threshold. The first test parameter indicator 258 comprises first test parameter indicator end 260 and a second test parameter end 262 of the first test parameter indicator 258. In this aspect, a test value representation 264 intersects the first test parameter indicator 258 at a second test parameter end 262 based on the test value exceeding the lower test parameter threshold. The test value representation 264 extends perpendicularly from the first test parameter indicator 258. In some aspects, the third summary label 256 may further comprise second test parameter indicator 270. In such aspects, the test value representation 264 can extend in a direction towards the second test parameter indicator 270. The first test parameter indicator 258 may be parallel with second test parameter indicator 270. In the illustration, first test parameter indicator 258 comprises a first test parameter indicator width 266, which is illustrated by theoretical dashed lines, while the test value representation 264 comprises test value representation width 268, also illustrated using theoretical dashed lines. In some cases, to emphasize the test value exceeding the lower test parameter threshold, the test value representation width 268 is greater than the test parameter indicator width 266. In aspects where there is the second test parameter indicator 270, the first test parameter indicator width 266 or the test value representation width 268 may be larger than the second test parameter indicator width, which has not been illustrated for simplicity. In some cases, the test value can be positioned between the first test parameter indicator 258 and the second test parameter indicator 270. In some aspects, the test value can be positioned adjacent to the first test parameter indicator 258.

Figure 2E:
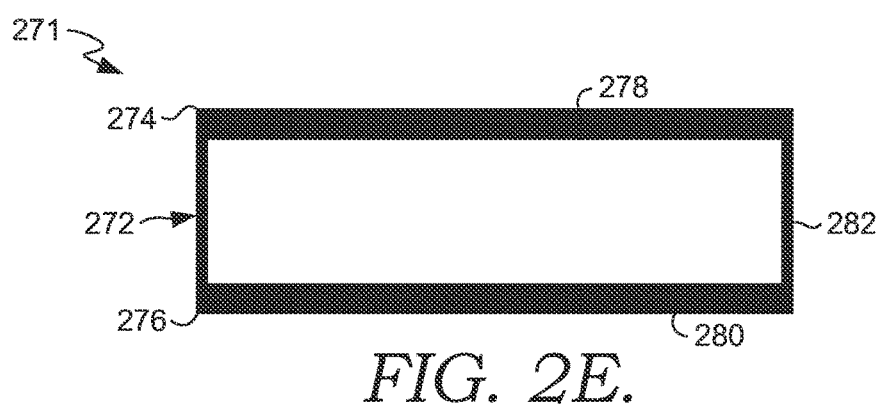

Referring now to FIG. 2E, a fourth summary label 271 that might be used to illustrate a critical test value. Here, a first test parameter indicator 272 comprises first test parameter indicator end 274 and a second test parameter indicator end 276. A first test value indicator 278 can intersect the first test parameter indicator 272 at the first test parameter indicator end 274 and extend perpendicularly away from the first test parameter indicator 274. A second test value indicator 280 can intersect the first test parameter indicator 272 at the second test parameter indicator end 276 and extend perpendicularly away from the first test parameter indicator 272. This embodiment may be used for test values that are critically high or critically low. In some aspects, the fourth summary label 271 comprises second parameter indicator 282 that is perpendicular to first parameter indicator 272. In such cases, the first test value indicator 278 or the second test value indicator 280 may extend from the first test parameter indicator 272 towards the second test parameter indicator 282. In some cases, a width of the first test value indicator 278 or the second test value indicator 280 may be greater than a width of the first test parameter indicator 272 or the second test parameter indicator 282 to emphasize the critical value on the upper and lower portions of fourth summary label 271, which allows the summary label to be compressed in the direction of the first test parameter indicator 272 and the second test parameter indicator 282 without losing the emphasis created by the different widths (not illustrated in this aspect).

Figure 4A:
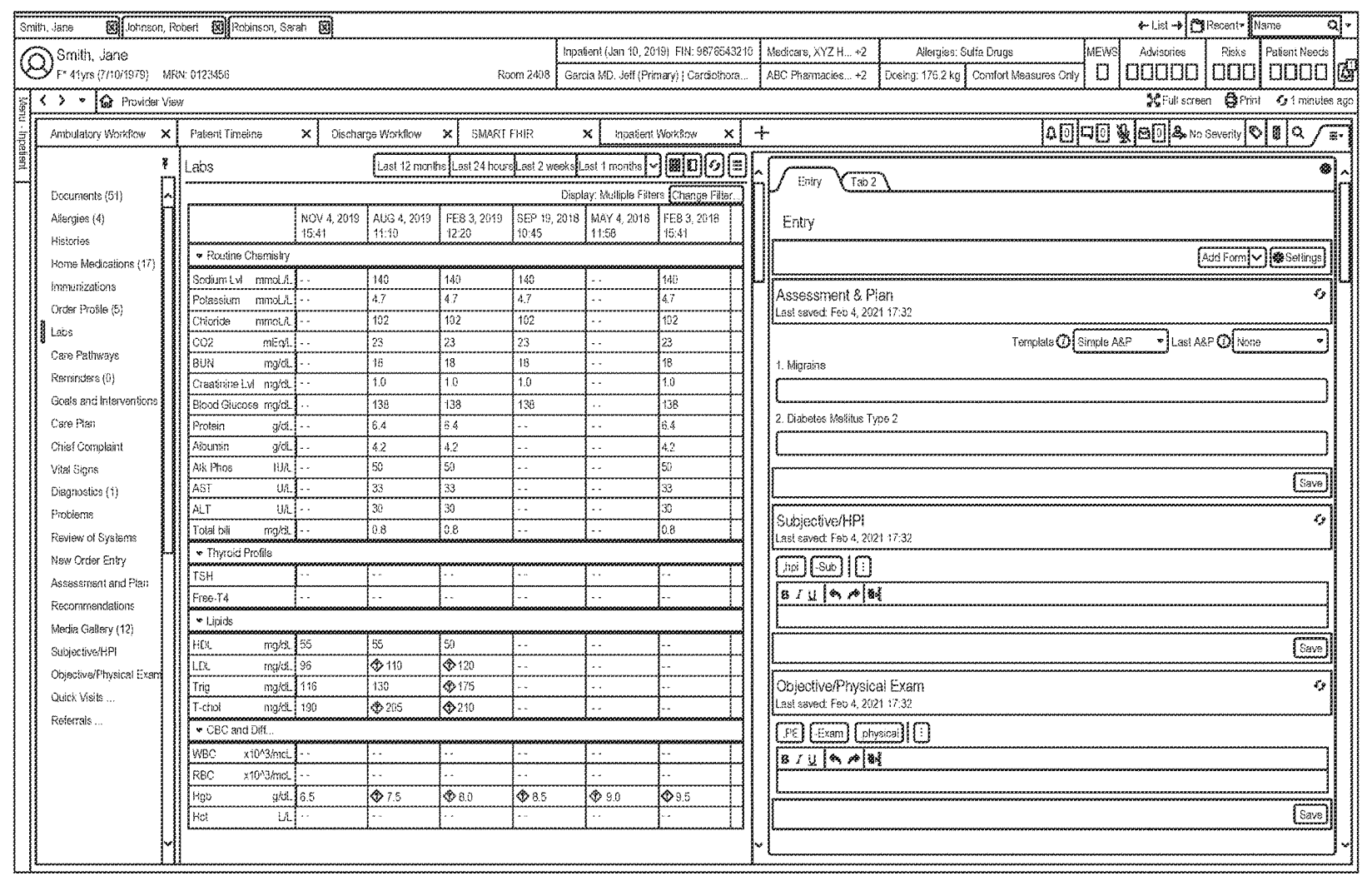
Figures 5A, 5B:
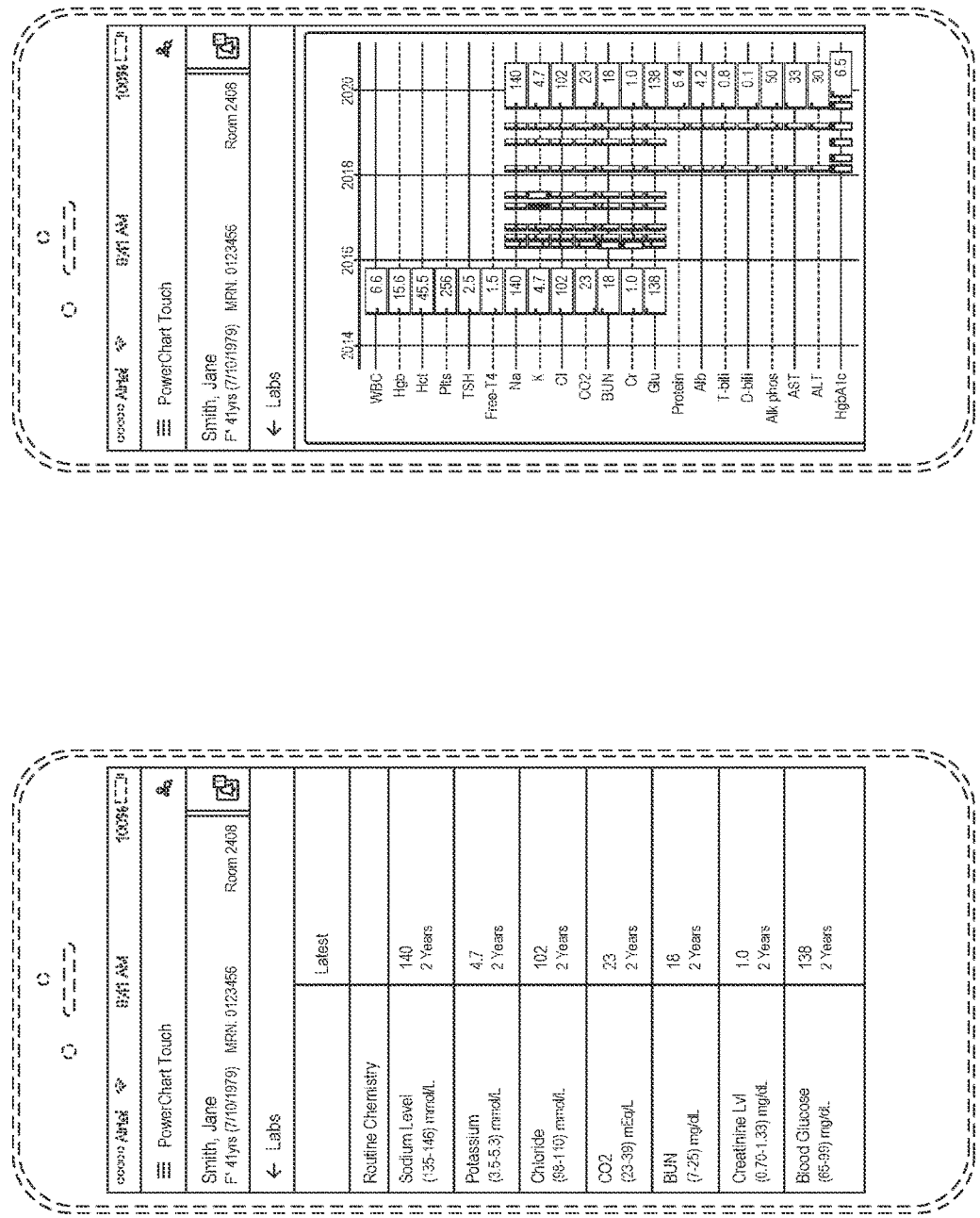
FIG. 5A illustrates an example prior art visualization graphical user interface displaying on a client smartphone.
FIG. 5B illustrates an example result visualization graphical user interface displaying on a client smartphone, in accordance with an aspect described herein.

When the summary labels are provided in conjunction with a timeline, the visual indication is more intuitive than traditional columnar displays (such as shown in FIGS. 4A and 5A).

As noted, and with some summary labels in general, the test value representation intersects the test parameter indicator at an intersection location. The intersection location may be between the first test parameter indicator end and the second test parameter indicator end, such as if the test value is within upper and lower parameter thresholds. The intersection location may proportionally represent the test value relative to the upper test parameter threshold and the test value relative to the lower test parameter threshold. Thus, the test value representation may indicate the result relative to the scale. Similarly, the test value representation widths may be used to distinguish whether the test values exceed an upper or lower parameter threshold or are critical. These test value representations may provide additional visibility to these test results being outside the prescribed threshold, while at the same time, provide for compressibility an expansion so that the same amount of information can be displayed on larger and smaller screens without having to zoom out, as in conventional methods, in manners that render the information too small to read on many smaller screens.

Figure 2F:
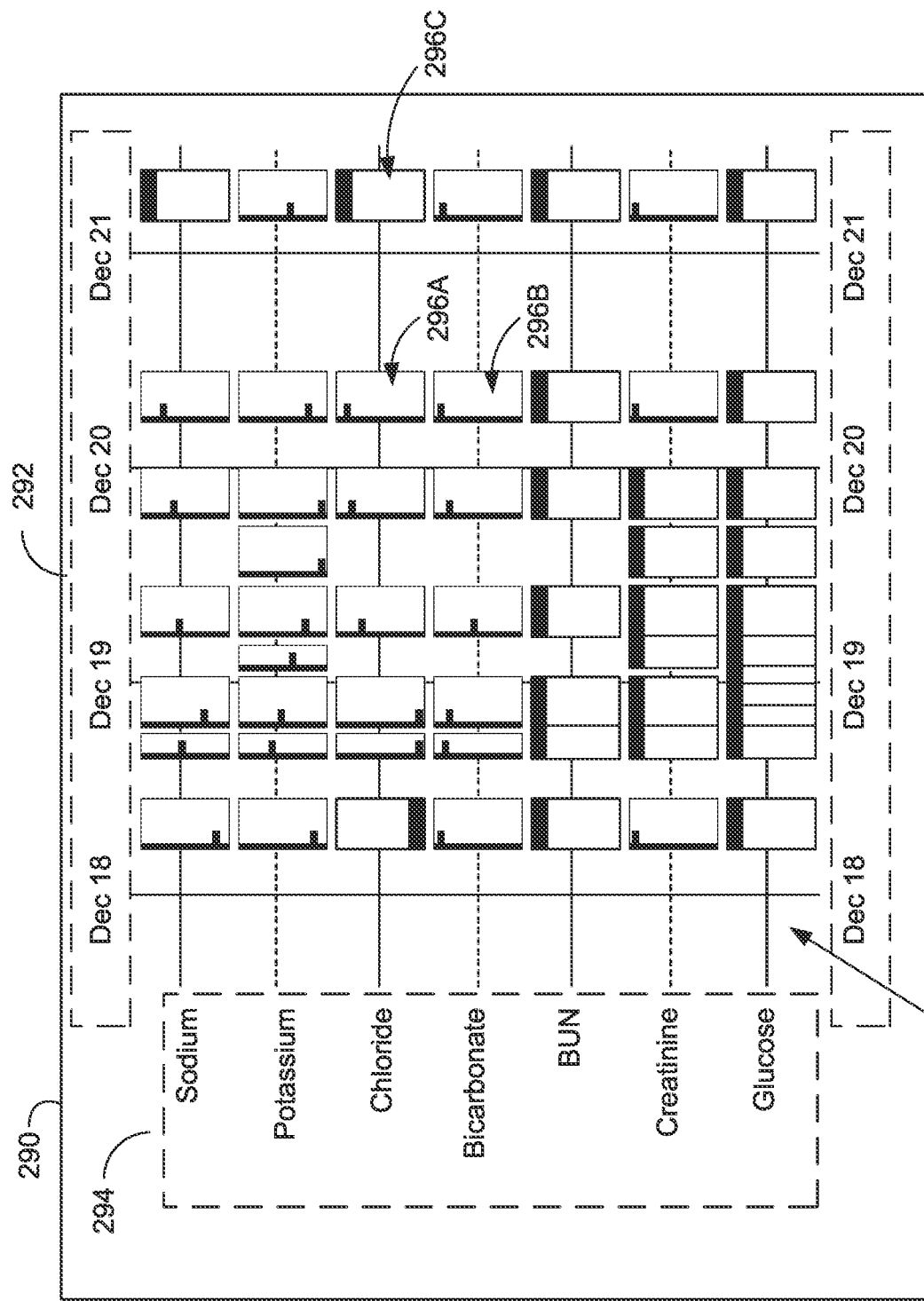
FIG. 2F is an example graphical user interface providing a timeline having summary labels for illustrating test results, in accordance with an aspect described herein.
Figure 3A:
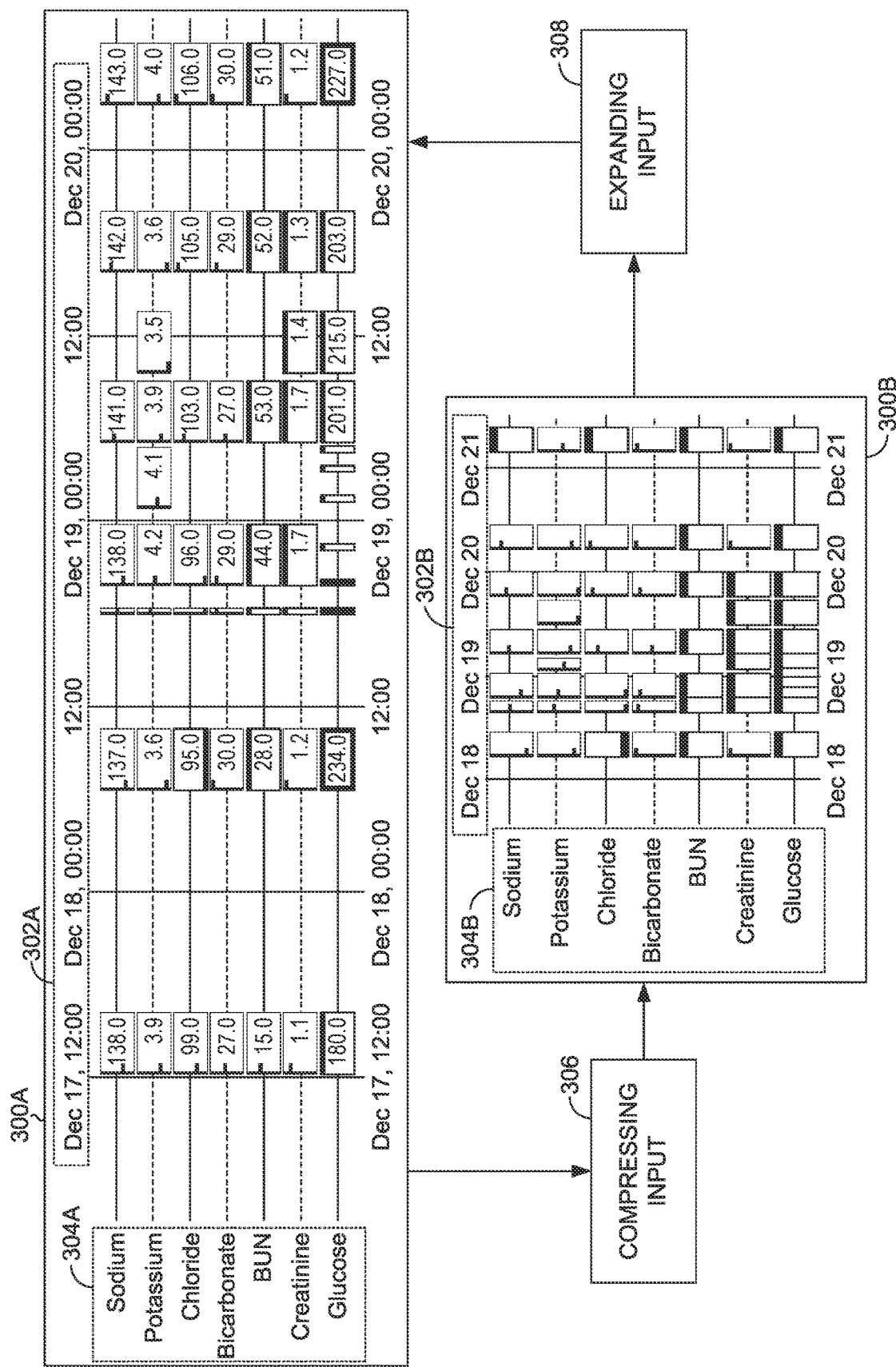
FIG. 3A illustrates expansion and compression of a timeline having summary labels for test results provided at a graphical user interface, in accordance with an aspect described herein.

Depending on the scale and the adjacent summary labels, the numerical representations of the test values may be added, abbreviated, or removed (as shown in FIG. 2F). The summary label provides information that summarizes the test result, making the numerical value less necessary to relay information. As such, some aspects of the present disclosure display numerical value if spacing or other settings allow, and it may be displayed based on screen size or the scale of the timeline, which will be described in more detail. FIG. 3A shows how the numerical value may be shown in an expanded timeline 302A and hidden in a compressed timeline 302B.

Two or more summary labels, such as a fifth summary label 296A, a sixth summary label 296B, and a seventh summary label 296C may be displayed on a graphical user interface 290, as shown in FIG. 2F. The fifth summary label 296A that corresponds to the same test time as the sixth summary label 296B may be aligned in a direction perpendicular to the direction of a timeline 292. If the fifth summary label 296A corresponds to a same test as the seventh summary label 296C, the fifth summary label 296A and the seventh summary label 296C may be aligned in a direction parallel to the timeline 292. A set of grid lines 298 may assist the user in determining how the summary labels, such as the fifth summary label 296A, the sixth summary label 296B, and the seventh summary label 296C, are aligned.

Turning back to FIG. 1, in general, the results plotter 118 generates a graphical plot and the GUI generator 119 creates a graphical user interface on a display 114 of the client device 104. The GUI generator 119 may generate any of the graphical user interfaces described herein.

With reference again to FIG. 3A, FIG. 3A shows an example graphical plot shown in a first timeline scale and a second timeline scale provided respectively at a first GUI 300A and a second GUI 300B. These may be generated by the GUI generator 119. More specifically, the timeline scales may include an expanded timeline scale 302A, a compressed timeline scale 302B, and any number of intermediate timeline scales. The user may select between the expanded timeline scale 302A and the compressed timeline scale 302B (including any intermediary scale between the example as shown in FIG. 3) by providing a compressing input 306 or an expanding input 308 at the input 116 of the client device 104. The expanded timeline scale 302A may allow for numerical values to be viewed along with greater fidelity in spacing along the expanded timeline 302A. The compressed timeline scale 302B may allow for an increased amount of information to be shown in a given screen size.

Prior to the compressing input 306, the GUI 300A comprises a first scale (for example, the expanded timeline scale 302A) of the timeline and a numerical representation associated with the test value adjacent to some of the test parameter indicators. After the compressing input 306, the first GUI 300A comprises the second scale 302B (for example, the compressed timeline scale 302A) of the timeline. In the second scale 302B, a greater timespan than the first scale of the timeline is displayed, as can be seen in FIG. 3A. In some instances, after the compressing input 306, the first GUI 300A does not comprise or include the numerical representation of the test value adjacent to the test parameter indicators, as can be seen in the compressed timeline scale 302B of FIG. 3A. Similarly, the numerical representation may be added following the expanding input 308 if the spacing allows.

Prior to the compressing input 306, the test value representation may have a first length as measured in the first direction. After the compressing input 306, the test value representation may have a second length as measured in the first direction, the second length being less than the first length. This allows the test value representation to be easier to see in the expanded timeline scale 302A while saving space in the compressed timeline scale 302B. Similarly, the test value representation may be elongated in the first direction upon an expanding input.

A length of the test value representation may be elongated or shortened based upon the scales, the relative distance between the two or more summary labels, or other considerations. An example of this is shown in FIG. 3A, in which it can be seen that in-range test value representations are shortened when moving from the expanded timeline scale 302A to the compressed timeline scale 302B. An elongated test value representation may be easier for the user to see, making reading of the summary label faster if space allows.

Each of graphical plots, as shown in FIG. 3A, include a timeline area (comprising timelines 302A and 302B) and a test label area (provide as test label area 304A and 304B). The graphical plot provides context for one or more summary labels therein. The timelines provide an indication as to when the associated test was performed. The test label area provides an indication of which test was performed. The timeline area extends horizontally in embodiments. The timeline area includes one or more time labels as shown in FIG. 3A. The time labels may include vertical reference lines on the graphical plot, such that the alignment between the time label and the test parameter indicator may be easily distinguished.

The test label area includes one or more test labels each associated with the test that was performed. The test label area extends vertically in some embodiments. Each test performed may be indicated by a test label. The test labels may include a shorthand name or other identifier for the test as a reference for the user. The test labels may be organized such that similar test types are adjacent, frequent tests are adjacent, tests related to a certain subject or condition are adjacent, or some other organization. The test labels may be selected for display (such as if the scale prevents all tests from being shown on the graphical plot) based upon similar criteria.

As used herein, a graphical plot scale may describe the area of a two-dimensional graphical plot or a one-dimensional element of the graphical plot, such as a length, height, width, radius, and the like. FIG. 3A further provides an example graphical user interface (such as the graphical user interfaces 300A and 300B) provided for display, such as at the display 114 of the client device 104. It will be understood that the graphical plot is illustrated only to describe the technology; however, nothing is meant to impart a visual requirement for the graphical plot. In some aspects, the graphical plot is not a visible part of the graphical user interface, but instead, is more theoretical in nature and defines an area of the graphical user interface. While timelines are shown comprising a portion of graphical plot area, a generated timeline may comprise any portion of or all of a graphical plot area.

Figure 3B:
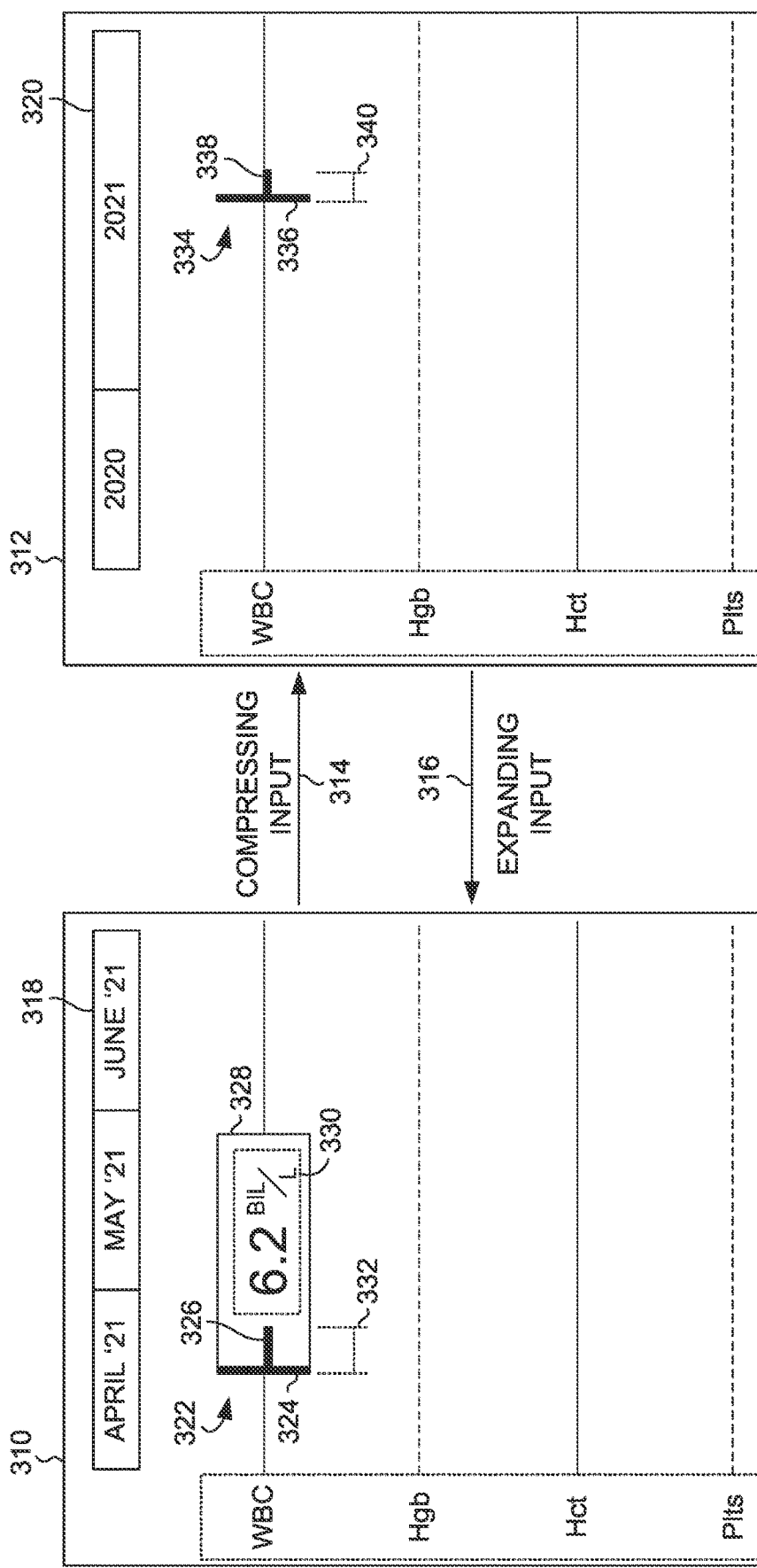
FIG. 3B illustrates an expanded summary label and a compressed summary label of a timeline, in accordance with an aspect described herein.

With reference now to FIG. 3B, expanded graphical user interface 310 and compressed graphical user interface 312 are provided to further illustrate summary expansion and compression of a summary label that can be done in a manner to provide the same information in a smaller area of a screen without losing context. As illustrated, the expanded graphical user interface 310 comprises expanded timeline 318. This may be presented in response to an expanding input 316. In this particular example, an area of the timeline has been expanded, and as such, a shorter time period is presented on the timeline. Here, an expanded summary label 322 comprises a test parameter indicator 324 and a test value representation 326 that extends away from the test parameter indicator 324. It will be realized that the expanded summary label 322 is provided only as an example and that any other embodiments of the present disclosure may be utilized as well. In expanded graphical user interface 310, the expanded summary label 322 also includes a second test parameter indicator 328 and a test result 330 positioned between the test parameter indicator 324 and the second test parameter indicator 328. Furthermore, in the expanded summary label 322, the first test value representation 326 has a first length 332, illustrated by theoretical dotted lines.

The compressed graphical user interface 312 illustrates a compressed summary label 334. This is displayed on the compressed timeline 320, which illustrates a second scale of a timeline that is greater that the first scale of the timeline relative to the expanded timeline 318. As will be understood, the compressed timeline 320 may illustrate the same timeline as the expanded timeline 318, just different scales. When the area is compressed based on a compressing input, a greater scale of the timeline is provided. The compressed summary label 334 corresponds to the expanded summary label 322 following a compressing input 314. Likewise, the expanded summary label 322 corresponds to the compressed summary label 334 following the expanding input 316. The compressed summary label 334 also comprises a test parameter indicator 336 and a second test value representation 338. The second test value representation 338 comprises a second length 340, illustrated by theoretical dotted lines. After the compressing input, the second length 340 is less than the first length 332. This allows more information to be presented on the timeline, thus allowing for the greater scale. Similarly, after the expanding input, the first length 332 is greater than the second length 340. Since the sale of the timeline is smaller, more contextual information associated with the expanded summary label 322 can be displayed, including the test value representation 338, illustrated here as a numerical representation.

In embodiments, the results plotter 118 generates a graphical plot proportional to a size of the display 114 of the client device 104. The size, as used herein, may consider physical size and dimensions, resolution, or other factors. For example, the graphical plot is generated as part of the graphical user interface 200 as created by the GUI generator 119. Thus, when the graphical user interface 200 is presented at the display 114 of the client device 104 (or other display), the presentation of the graphical plot will be proportional.

In embodiments, the results plotter 118 may determine the display size of the display 114 of the client device 104, determine the timeline scale for two or more test results, and adjusts the scale proportional to the display 114 of the client device 104. This may include compressing or expanding the timeline 206 as shown in FIG. 2A.

The results plotter 118 may determine the size of the display device or the graphical plot scale. The dimensions of the display device or the graphical plot can be measured in pixels ("px"). This unit of measurement is roughly equivalent to 1/96 of an inch or 0.26 millimeters. In an aspect, the results plotter 118 generates a graphical plot for a graphical user interface, such as the GUI 200, in response to detecting a change in size of the display device. This may occur where a user logs onto another device having a different display device, or where the user changes an orientation of a display device, such that it changes an aspect ratio of the display device. An example of this would be the user rotating a mobile device, which may have a non-square display, to a different position, such as landscape to portrait or vice versa. In such cases, the results plotter 118 can update a graphical plot scale based on a change in display device or orientation of the display device.

Figures 6A, 6B:
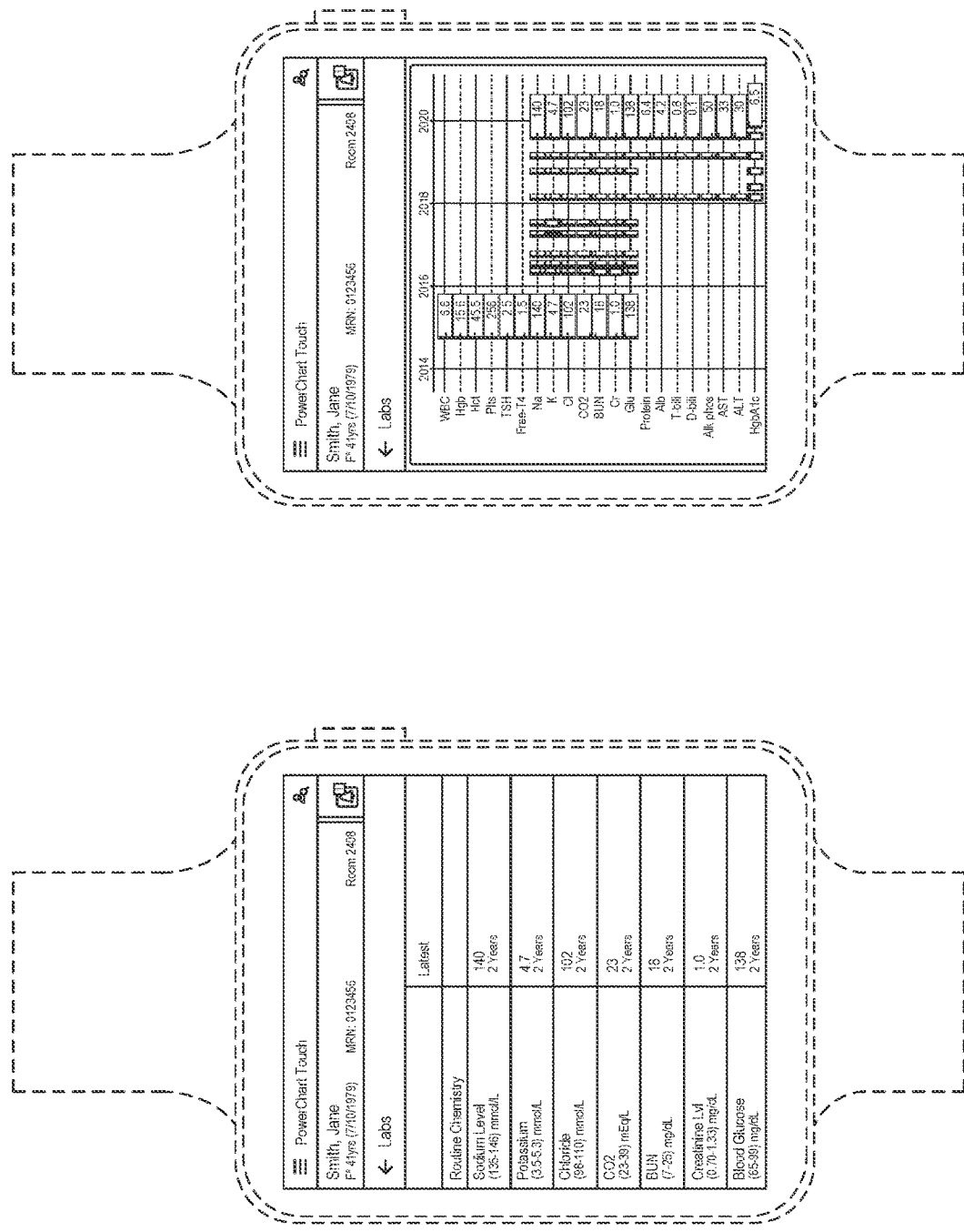
FIG. 6A illustrates an example prior art visualization graphical user interface displaying on a client smart watch.
FIG. 6B illustrates an example result visualization graphical user interface displaying on a client smart watch, in accordance with an aspect described herein.

FIGS. 4A-6B shows various traditional views compared with embodiments of the present disclosure, as shown on various screen sizes. FIGS. 4A and 4B show a difference between a traditional columnar display of test results (FIG. 4A) and an embodiment of the present disclosure having summary labels associated with the test values (FIG. 4B) as shown on a computer display. FIGS. 5A and 5B show differences between a traditional columnar display of test results (FIG. 5A) and an embodiment of the present disclosure having summary labels associated with the test values (FIG. 5B) as shown on a smartphone display. FIGS. 6A and 6B show a difference between a traditional columnar display of test results (FIG. 6A) and an embodiment of the present disclosure having summary labels associated with the test values (FIG. 6B) as shown on a smart watch display. As can be seen, the prior art figures convey significantly less information in a less intuitive way. This would prevent the user from obtaining needed information from the single graphical plot of the test results.

Figure 4B:
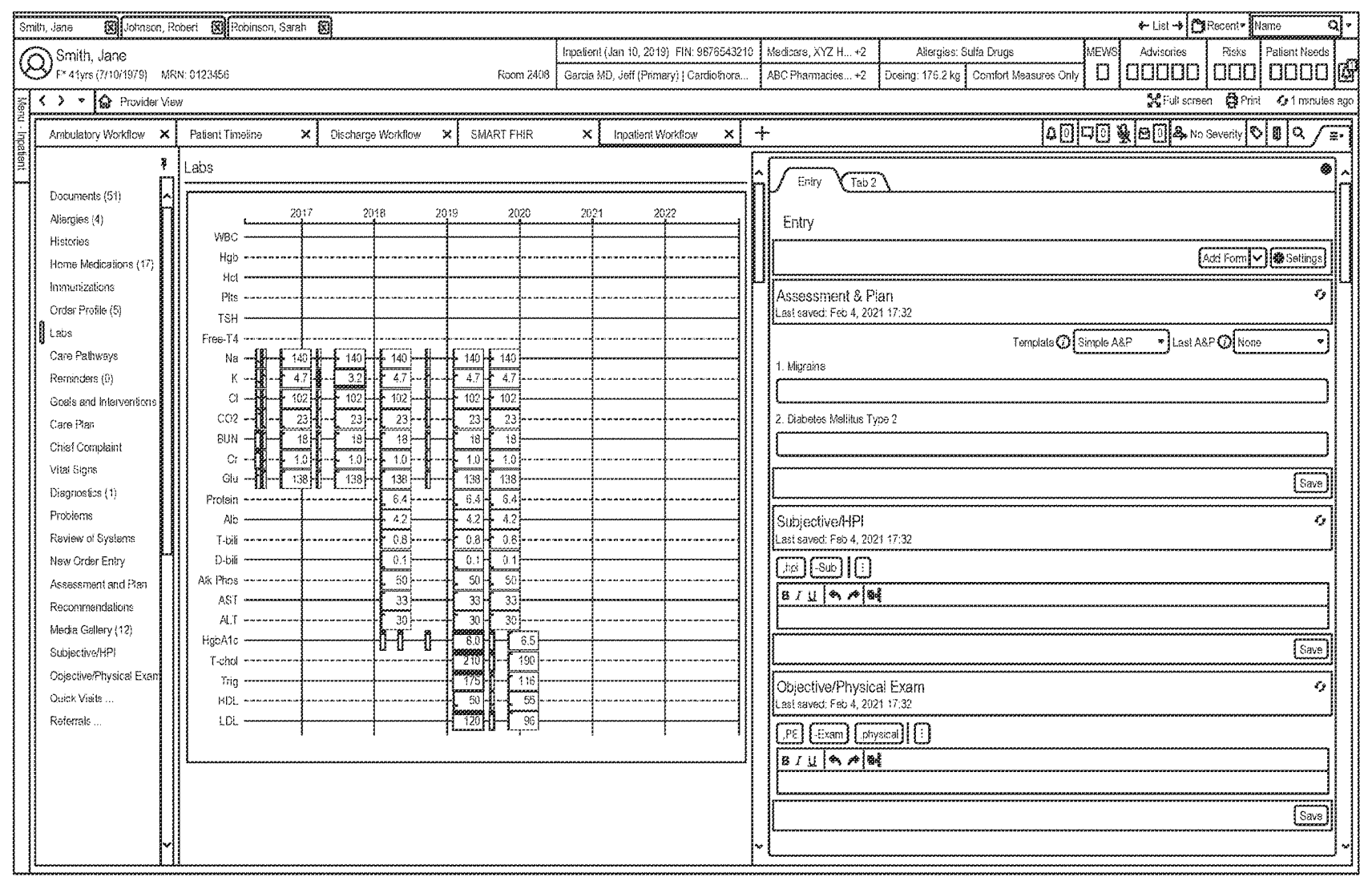

Various advantages of embodiments of the present disclosure may be ascertained by comparing the prior art FIGS. 4A, 5A, and 6A) with a corresponding embodiment FIGS. 4B, 5B, and 6B, respectively). The columnar displays figures convey significantly less information in a less intuitive way. The user must look at the column heading to get an appreciation for the time spacing between the columns and keep this in mind while looking at the respective values. Some values of the columnar display may be emphasized as being significantly out of range, but there is no information provided relative to the other test results as to where the test results fall within a normal range. The test parameter indicators and the test value representations (as labeled in FIG. 2B) thus provide a technical advantage over the prior art columnar displays because they convey information in an intuitive way that was not possible using traditional methods. Embodiments of the present disclosure improve the computer functionality by increasing the amount of information, as well as the context for that information, that can be displayed on a given screen size. Embodiments of the present disclosure also allow the same or greater amount of information, as well as the context for that information, to be shown on a smaller screen size. This allows for portability of the information that was not possible using traditional methods. A user of a traditional columnar display would have to manipulate the smaller screens to move across the horizon to view the information that can be viewed in a single graphical user interface using the methods described herein. In the existing method, even if zooming out to see more data, loses the context so that the user cannot ascertain the values or whether they are high or low relative to the thresholds.

Turning back to FIG. 1, in general, the results plotter 118 determines a timeline. To determine the timeline, the results plotter 118 can receive, access, or otherwise acquire information that has associated dates or times, such as time stamps, associated with the one or more tests. The results plotter 118 can determine a chronological order of the received information based on the associated dates or times. In an aspect, the results plotter 118 receives a timeline from another application, receives information having a chronological order, or receives information and determines the chronological order of the received information. In this way, the results plotter 118 may add additional information to an existing timeline.

The timeline determined by the results plotter 118 includes a scale associated with a length of time representation. As noted above, the length of time represented by the timeline can be all or a portion of a range of time provided by received chronological information. In an aspect, the received information includes test results from electronic medical record information for a patient, and the determined timeline represents all or a portion of the test results in the patient's medical history. The length of time representation may include any range of time. Some examples might be 1 hour, 24 hours, 7 days, 30 days, 90 days, 1 year, 4 years, and so forth. The scale selected may be based at least in part on a screen size of the display device, such as the computer of FIG. 4B, the smart phone of FIG. 5B, or the smart watch of FIG. 6B. The scale may also be updated by the user through user input.

As noted previously, the graphical plot is generated proportionally to the screen size. Thus, where the screen size is larger, the graphical plot will be larger in many cases, as well. This includes the size of the display device within a single group, such as the small devices. For instance, a graphical plot may be smaller on a display device of a small smartphone measuring 2.5 cm×9.5 cm than it will be on a small smartphone measuring 6.5 cm×16.5 cm. Since the graphical plot scale increases with the size of the screen, scale of the presented timeline can be determined by the results plotter 118 based on the graphical plot scale as it relates to the category of display device. In another embodiment, the graphical plot scale may be defined based on the display device size. For example, for small display devices, the graphical plot scale can be equal to or within the range of 558px-890px; for medium size display devices, the graphical plot scale can be equal to or within the range of 891px-1334px, and for a large display device, the graphical plot scale can be equal to or greater than 1335px. In another embodiment, an extra small display device may be defined. In such cases, the graphical plot scale for an extra small display device might be equal to or less than 557px. In another example, the graphical plot scale of the extra small display device may be equal to or within 284px-557px. Thus, in one example, as the display device size increases, the graphical plot scale may increase within the defined range. In another example, the display device size for a category (small, medium, large, etc.) may increase or decrease while the graphical plot scale for that category remains at a fixed size, such as a size within the defined range. Both of these examples represent graphical plots that are generated proportional to the display device.

The input analyzer 120 receives user input from the input 116 of the client device 104 or other computing device. For example, the user may input a pinching motion onto a touchscreen display of the client device 104. The input analyzer 120 determines a change in scale based upon that user input. The user input may provide a date range to be used as a scale. For example, the user may input (such as via a keyboard as the input 116) a starting and ending date or time for the display. This may allow the user to quickly select test results from a specific instance (such as when the patient arrived at the hospital, for example). The scale adjuster 122 adjusts the scale on graphical plot. For example, if the second scale shows a greater time span, the scale adjuster 122 may compress the test value representation 218 when updating the first scale to the second scale. Similarly, if the second scale shows a lesser time span, the scale adjuster 122 may expand the test value representation 218 (see FIG. 2A) when updating the first scale to the second scale.

Figure 7:
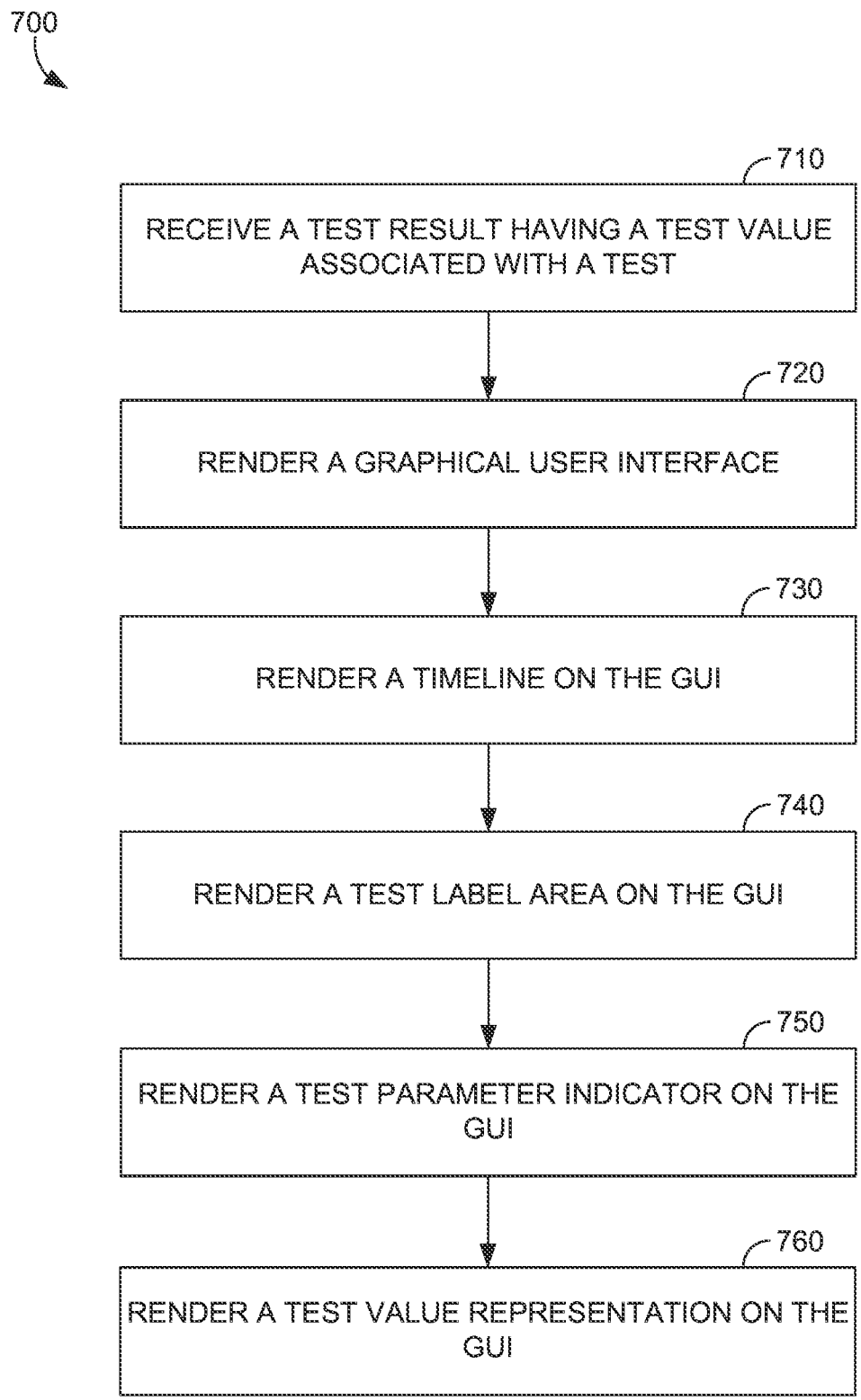
FIG. 7 is a flow diagram of an example method for generating a result visualization in accordance with an aspect described herein.
Figure 8:
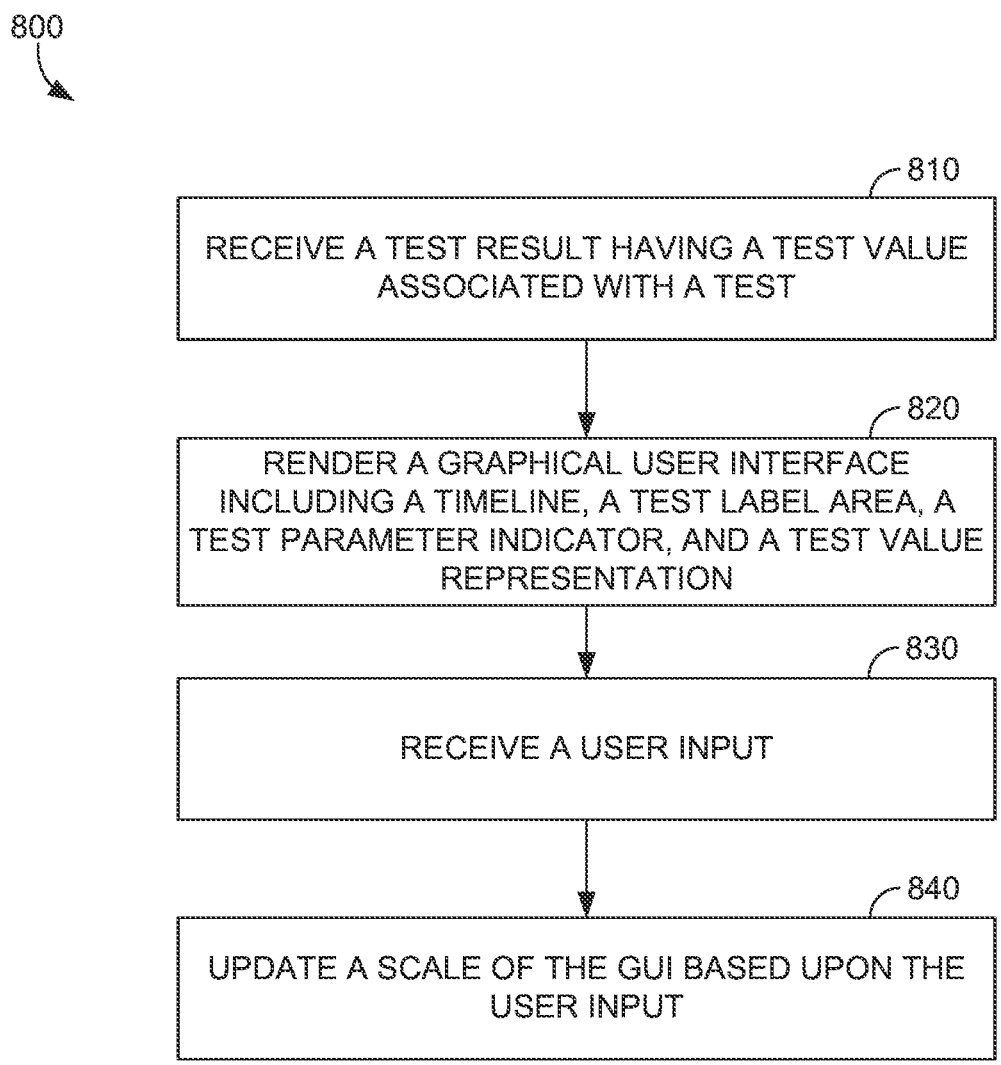
FIG. 8 is a flow diagram of an example method for generating and updating a scale of a result visualization, in accordance with an aspect described herein.

With reference now to FIGS. 7-8, flow diagrams are provided illustrating methods 700 and 800, respectively. Each block of the methods, and any other methods described herein, can comprise a computing process performed using any combination of hardware, firmware, or software. For instance, various functions can be carried out by a processor executing instructions stored in memory. The methods 700 and 800 can also be embodied as computer-usable instructions stored on computer storage media. The methods 700 and 800 can be provided by a standalone application, a service or hosted service (standalone or in combination with another hosted service), or a plug-in to another product, to name a few. The methods 700 and 800 may be implemented by the result visualization system 102 as described in conjunction with at least FIGS. 1-6.

Turning initially to FIG. 7, a flow diagram of the method 700 for providing a graphical plot at a display device, is illustrated. At block 710, the method 700 may include receiving a test result comprising a test value, the test result being associated with a test comprising an upper test parameter threshold and a lower test parameter threshold. At block 720, the method 700 may include rendering a graphical user interface on a display at a first scale based upon a screen size of the display.

At block 730, the method 700 may include rendering a timeline on the GUI. The timeline extends in a first direction 202 of the graphical user interface. The timeline may include one or more date or time representations indicative of when the test was performed.

At block 740, the method 700 may include rendering a test label area on the GUI. The test label area includes a test label associated with the test, the test label area extending in a second direction 204 of the graphical user interface, the second direction 204 being perpendicular to the first direction 202. The test label area is indicative of the test types that were performed.

At block 750, the method 700 may include rendering a test parameter indicator associated with the test on the GUI. The test parameter indicator is provided at a location corresponding with the test label of the test label area and with a location corresponding to a test time of the timeline. The test parameter indicator extends in the second direction of the graphical user interface from a first test parameter indicator end associated with the upper test parameter threshold to a second test parameter indicator end associated with a lower test parameter threshold.

At block 760, the method 700 may include rendering a test value representation of the test value extending away from the test parameter indicator in the second direction 204 of the graphical user interface, the test value representation intersecting the test parameter indicator between the first test parameter indicator end and the second test parameter indicator end, wherein an intersection location proportionally represents the test value relative to the upper test limit and the test value to the lower test limit. In some instances, the test value representation is enlarged in at least one of the first direction or the second direction at the upper test parameter end to indicate that the test value exceeds the upper test parameter threshold. In some instances, a numerical value associated with the test value is displayed along the test parameter representation.

In some instances, the GUI may display a second test parameter indicator and a second test value representation for a second test value on the timeline based upon a second test time of the second test result. If the second test is the same as the first test, the second test value representation is aligned with the test label associated with the first test. If the second test is different from the first test, the second test value representation is aligned with a second test label associated with the second test. The second test label is located in the test label area extended in the second direction.

Referencing now FIG. 8, the figure illustrates a flow diagram of a method 800 for determining and displaying an updated graphical plot. At block 810, the method 800 may include receiving a test result having a test value associated with a test. At block 820, the method 800 may include rendering a graphical user interface including a timeline, a test label area, a test parameter indicator, and a test value representation. At block 830, the method 800 may include receiving a user input. At block 840, the method 800 may include updating a scale of the GUI based upon the user input. This may include determining whether to add or remove a numerical representation of the test value from the graphical user interface based upon the first scale and the second scale and determining whether to compress or expand the test value representation in the first direction based upon the first scale and the second scale.

Having described an overview of embodiments of the present technology, an example operating environment in which embodiments of the present technology may be implemented is described below in order to provide a general context for various aspects. Referring now to FIG. 9, in particular, an exemplary operating environment for implementing embodiments of the present disclosure is shown and designated generally as the computing device 900. The computing device 900 is but one example of a suitable computing environment and is not intended to suggest any limitation as to the scope of use or functionality of the present disclosure. Neither should the computing device 900 be interpreted as having any dependency or requirement relating to any one or combination of components illustrated.

The present disclosure may be described in the general context of computer code or machine-useable instructions, including computer-executable instructions such as program modules, being executed by a computer or other machine, such as a cellular telephone, personal data assistant or other handheld device. Generally, program modules including routines, programs, objects, components, data structures, etc., refer to code that perform particular tasks or implement particular abstract data types. The present disclosure may be practiced in a variety of system configurations, including hand-held devices, consumer electronics, general-purpose computers, more specialty computing devices, etc. The present disclosure may also be practiced in distributed computing environments where tasks are performed by remote-processing devices that are linked through a communications network.

Figure 9:
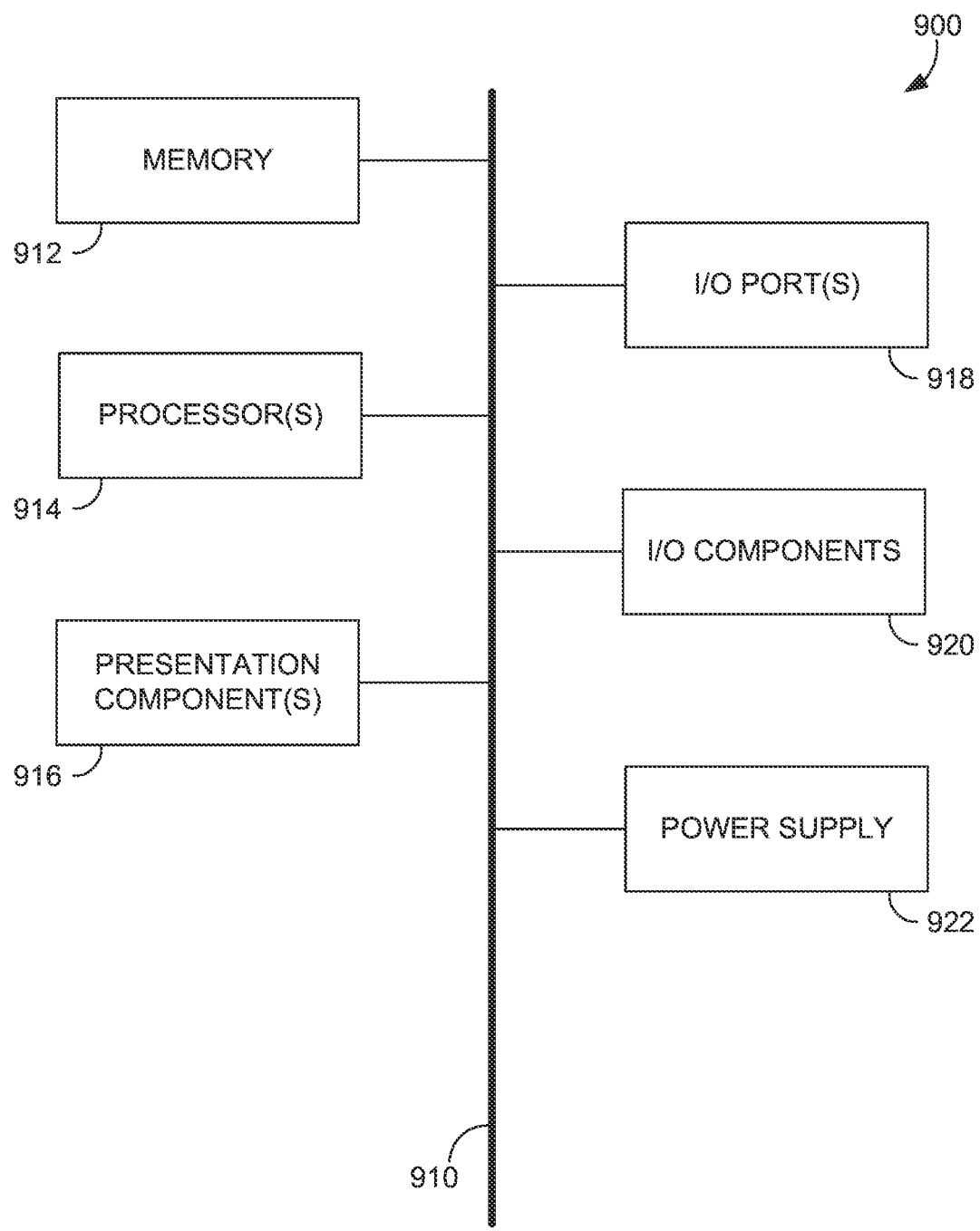
FIG. 9 is a block diagram of an example operating environment in which embodiments of the present technology may be employed.

With reference to FIG. 9, the computing device 900 includes a bus 910 that directly or indirectly couples the following devices: a memory 912, one or more processors 914, one or more presentation components 916, input/output (I/O) port(s) 918, input/output (I/O) components 920, and a power supply 922. The bus 910 represents what may be one or more busses (such as an address bus, data bus, or combination thereof). Although the various blocks of FIG. 9 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventor recognizes that such is the nature of the art and reiterates that the diagram of FIG. 9 is merely illustrative of an exemplary computing device that can be used in connection with one or more embodiments of the present disclosure. Distinction is not made between such categories as "workstation," "server," "laptop," "hand-held device," etc., as all are contemplated within the scope of FIG. 9 and reference to the "computing device."

The computing device 900 typically includes a variety of computer-readable media. The computer-readable media can be any available media that can be accessed by the computing device 900 and includes both volatile and nonvolatile media, and removable and non-removable media. By way of example, and not limitation, the computer-readable media may comprise computer storage media and communication media. The computer storage media includes both volatile and nonvolatile, removable, and non-removable media implemented in any method or technology for storage of information such as computer-readable instructions, data structures, program modules or other data. The computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information, and which can be accessed by the computing device 900. The computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media.

The memory 912 includes computer-storage media in the form of volatile or nonvolatile memory. The memory 912 may be removable, non-removable, or a combination thereof. Exemplary hardware devices include solid-state memory, hard drives, optical-disc drives, etc. The computing device 900 includes one or more processors 914 that read data from various entities such as the memory 912 or the I/O components 920. The presentation component(s) 916 present data indications to a user or other device. Exemplary presentation components include a display device, speaker, printing component, vibrating component, etc.

The I/O port(s) 918 allow the computing device 900 to be logically coupled to other devices including the I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 900. The computing device 900 may be equipped with depth cameras, such as stereoscopic camera systems, infrared camera systems, RGB camera systems, touchscreen technology, and combinations of these, for gesture detection and recognition. Additionally, the computing device 900 may be equipped with accelerometers or gyroscopes that enable detection of motion. The output of the accelerometers or gyroscopes may be provided to the display of the computing device 900 to render immersive augmented reality or virtual reality.

Embodiments described herein support result visualization that maintains context and provides information in an intuitive manner. The components described herein refer to integrated components of the visualization generation system 102. The integrated components refer to the hardware architecture and software framework that support functionality using the product determination system. The hardware architecture refers to physical components and interrelationships thereof and the software framework refers to software providing functionality that can be implemented with hardware embodied on a device.

The end-to-end software-based result visualization system can operate within the result visualization components to operate computer hardware to generate intuitive timelines that maintain context. At a low level, hardware processors execute instructions selected from a machine language (also referred to as machine code or native) instruction set for a given processor. The processor recognizes the native instructions and performs corresponding low-level functions relating, for example, to logic, control, and memory operations. Low-level software written in machine code can provide more complex functionality to higher levels of software. As used herein, computer-executable instructions include any software, including low level software written in machine code, higher level software such as application software and any combination thereof. In this regard, the result visualization system components can manage resources and provide services for the system's functionality. Any other variations and combinations thereof are contemplated with embodiments of the present disclosure.

Having identified various components in the present disclosure, it should be understood that any number of components and arrangements may be employed to achieve the desired functionality within the scope of the present disclosure. For example, the components in the embodiments depicted in the figures are shown with lines for the sake of conceptual clarity. Other arrangements of these and other components may also be implemented. For example, although some components are depicted as single components, many of the elements described herein may be implemented as discrete or distributed components or in conjunction with other components, and in any suitable combination and location. Some elements may be omitted altogether. Moreover, various functions described herein as being performed by one or more entities may be carried out by hardware, firmware, or software, as described below. For instance, various functions may be carried out by a processor executing instructions stored in memory. As such, other arrangements, and elements (for example, machines, interfaces, functions, orders, and groupings of functions, etc.) can be used in addition to or instead of those shown.

Embodiments described above may be combined with one or more of the specifically described alternatives. In particular, an embodiment that is claimed may contain a reference, in the alternative, to more than one other embodiment. The embodiment that is claimed may specify a further limitation of the subject matter claimed.

The subject matter of the present disclosure is described with specificity herein to meet statutory requirements. However, the description itself is not intended to limit the scope of the present disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" or "block" might be used herein to connote different elements of methods employed, the terms should not be interpreted as implying any particular order among or between various steps herein disclosed unless and except when the order of individual steps is explicitly stated.

Within this disclosure, "communicating" and "in communication" have the same broad meaning as the word "receiving," or "transmitting" facilitated by software or hardware-based buses, receivers, or transmitters" using communication media described herein. Also, the word "initiating" has the same broad meaning as the word "executing or "instructing" where the corresponding action can be performed to completion or interrupted based on an occurrence of another action. In addition, words such as "a" and "an," unless otherwise indicated to the contrary, include the plural as well as the singular. Thus, for example, the constraint of "a feature" is satisfied where one or more features are present. Also, the term "or" includes the conjunctive, the disjunctive, and both (a or b thus includes either a or b, as well as a and b).

For purposes of a detailed discussion above, embodiments of the present technology described with reference to a distributed computing environment; however, the distributed computing environment depicted herein is merely an example. Components can be configured for performing novel aspects of embodiments, where the term "configured for" can refer to "programmed to" perform particular tasks or implement particular abstract data types using code. Further, while embodiments of the present technology may generally refer to the result visualization system, it is understood that the techniques described may be extended to other implementation contexts.

From the foregoing, it will be seen that this technology is one well adapted to attain all the ends and objects described above, including other advantages that are obvious or inherent to the structure. It will be understood that certain features and sub-combinations are of utility and may be employed without reference to other features and sub-combinations. This is contemplated by and is within the scope of the claims. Since many possible embodiments of the described technology may be made without departing from the scope, it is to be understood that all matter described herein or illustrated the accompanying drawings is to be interpreted as illustrative and not in a limiting sense.

What is claimed:

1. A system for displaying test results, the system comprising:
   at least one processor;
   and one or more computer readable storage media having computer-executable instructions embodied thereon that, when executed by the at least one processor, cause the at least one processor to:
   access a test result comprising a test value, the test result being associated with a test comprising an upper test parameter threshold and a lower test parameter threshold;
   render a graphical user interface (GUI) comprising:
   a timeline extending in a first direction of the GUI;
   a test label area comprising a test label associated with the test, the test label area extending in a second direction of the GUI, the second direction being perpendicular to the first direction;
   a first test parameter indicator associated with the test provided at a location corresponding with the test label of the test label area, and with a location corresponding to a test time of the timeline, the first test parameter indicator extending in the second direction from a first test parameter indicator end associated with the upper test parameter threshold to a second test parameter indicator end associated with the lower test parameter threshold;
   a second test parameter indicator parallel to and spaced apart from the first test parameter indicator;
   and a test value representation of the test value beginning at the first test parameter indicator and extending in the first direction towards the second test parameter indicator, wherein in response to the test value being at or between the upper test parameter threshold and the lower test parameter threshold:
   the test value representation being displayed as intersecting the first test parameter indicator at or between the first test parameter indicator end and the second test parameter indicator end, wherein an intersection location proportionally represents the test value relative to the upper test parameter threshold and the test value relative to the lower test parameter threshold, and the test value representation extending towards but not connecting with the second test parameter indicator to visually represent a threshold not being exceeded;
   and wherein in response to the test value exceeding the upper test parameter threshold or the lower test parameter threshold:
   the test value representation being displayed as intersecting the first test parameter indicator at an intersection location at the first test parameter indicator end or at the second test parameter indicator end, and the test value representation extending to connect with the second test parameter indicator to visually represent a threshold being exceeded;
   and provide the rendered GUI for display at a display of a computing device.

2. The system of claim 1, wherein the system is configured to, in response to the test value representation intersecting the first test parameter indicator at the first test parameter indicator end based on the test value exceeding the upper test parameter threshold, display the test value representation having a test value representation width measured in the second direction that is greater than a test parameter indicator width, of the first test parameter indicator, measured in the first direction.

3. The system of claim 1, wherein the system is configured to, in response to the test value representation intersecting the first test parameter indicator at the second test parameter indicator end based on the test value exceeding the lower test parameter threshold, display the test value representation having a test value representation width measured in the second direction that is greater than a test parameter indicator width, of the first test parameter indicator, as measured in the first direction.

4. The system of claim 1, wherein the GUI further comprises a numerical value associated with the test value adjacent to the first test parameter indicator, and wherein the at least one processor is further caused to:
   receive a compressing input;
   modify a first scale of the timeline to a second scale of the timeline, the second scale of the timeline comprising a greater timespan than the first scale; and
   based on the modification from the first scale to the second scale of the timeline, remove the numerical value associated with the test value.

5. The system of claim 1, wherein the at least one processor is further caused to:
   receive a compressing input; and
   based on the compressing input, modify a first length of the test value representation to a second length of the test value representation, the second length being less than the first length, and the first length and the second length being measured in the first direction.

6. One or more computer storage media having computer-executable instructions embodied thereon that, when executed by a processor, cause the processor to generate a graphical user interface (GUI) for displaying test results at a computing device, the GUI comprising:
   a timeline extending in a first direction of the GUI;
   a test label area comprising a test label associated with a test, the test label area extending in a second direction of the GUI, the second direction being perpendicular to the first direction, wherein the test is associated with an upper test parameter threshold and a lower test parameter threshold, and wherein the test is associated with a test result comprising a test value;
   a first test parameter indicator associated with the test provided at a location corresponding with the test label of the test label area, and with a location corresponding to a test time of the timeline, the first test parameter indicator extending in the second direction from a first test parameter indicator end associated with the upper test parameter threshold to a second test parameter indicator end associated with the lower test parameter threshold;

a second test parameter indicator parallel to and spaced apart from the first test parameter indicator;

and a test value representation of the test value beginning at the first test parameter indicator and extending in the first direction towards the second text parameter indicator, wherein in response to the test value being at or between the upper test parameter threshold and the lower test parameter threshold:

the test value representation intersecting the first test parameter indicator at or between the first test parameter indicator end and the second test parameter indicator end, wherein an intersection location proportionally represents the test value relative to the upper test parameter threshold and the test value relative to the lower test parameter threshold, and the test value representation extending towards but not connecting with the second test parameter indicator to visually represent a threshold not being exceeded;

and wherein in response to the test value exceeding the upper test parameter threshold or the lower test parameter threshold:

the test value representation being displayed as intersecting the first test parameter indicator at an intersection location at the first test parameter indicator end or at the second test parameter indicator end, and extending to connect with the second test parameter indicator to visually represent a threshold being exceeded.

7. The media of claim 6, wherein in response to the test value exceeding the upper test parameter threshold, the test value representation is displayed having a test value representation width measured in the second direction that is greater than a test parameter indicator width, of the first test parameter indicator, measured in the first direction.

8. The media of claim 7, wherein the test value representation width is greater than a second test parameter indicator width of the second test parameter indicator as measured in the first direction.

9. The media of claim 7, wherein the GUI further comprises the test value positioned adjacent to the first test parameter indicator.

10. The media of claim 6, wherein in response to the test value exceeding the lower test parameter threshold, the test value representation is displayed having a test value representation width measured in the second direction that is greater than a test parameter indicator width, of the first test parameter indicator, as measured in the first direction.

11. The media of claim 10, wherein the test value representation width is greater than a second test parameter indicator width of the second test parameter indicator as measured in the first direction.

12. The media of claim 10, wherein the GUI further comprises the test value positioned adjacent to the first test parameter indicator.

13. The media of claim 6, wherein prior to a compressing input, the GUI comprises a first scale of the timeline and a numerical value associated with the test value adjacent to the first test parameter indicator, and wherein after the compressing input, the GUI comprises a second scale of the timeline, the second scale comprising a greater timespan than the first scale of the timeline, and wherein after the compressing input the GUI does not comprise the test value adjacent to the first test parameter indicator.

14. The media of claim 6, wherein prior to a compressing input, the test value representation comprises a first length as measured in the first direction, and wherein after the compressing input, the test value representation comprises a second length as measured in the first direction, the second length being less than the first length.

15. The media of claim 6, wherein prior to an expanding input, the test value representation comprises a first length as measured in the first direction, and wherein after the expanding input, the test value representation comprises a second length as measured in the first direction, the second length being greater than the first length.

16. A computerized method for displaying test results performed by at least one processor, the computerized method comprising:

receiving a test result comprising a test value, the test result being associated with a test comprising an upper test parameter threshold and a lower test parameter threshold;

and generating a graphical user interface (GUI) for presentation at a display, the GUI comprising:

a timeline extending in a first direction of the GUI;

a test label area comprising a test label associated with the test, the test label area extending in a second direction of the GUI, the second direction being perpendicular to the first direction;

a first test parameter indicator associated with the test provided at a location corresponding with the test label of the test label area, and with a location corresponding to a test time of the timeline, the first test parameter indicator extending in the second direction from a first test parameter indicator end associated with the upper test parameter threshold to a second test parameter indicator end associated with the lower test parameter threshold;

a second test parameter indicator parallel to and spaced apart from the first test parameter indicator;

and a test value representation of the test value;

wherein in response to the test value being at or between the upper test parameter threshold and the lower test parameter threshold:

the test value representation is displayed beginning at the first test parameter indicator and extending in the first direction towards the second test parameter indicator, the test value representation being displayed as intersecting the first test parameter indicator between the first test parameter indicator end and the second test parameter indicator end, wherein an intersection location proportionally represents the test value relative to the upper test parameter threshold and the test value to the lower test parameter threshold, and the test value representation extending towards but not connecting with the second test parameter indicator to visually represent a threshold not being exceeded;

and wherein in response to the test value exceeding the upper test parameter threshold or the lower test parameter threshold:

the test value representation being displayed as intersecting the first test parameter indicator at an intersection location at the first test parameter indicator end or at the second test parameter indicator end, and the test value representation extending to connect with the second test parameter indicator to visually represent a threshold being exceeded.

17. The computerized method of claim 16, wherein in response to the test value exceeding the upper test parameter threshold, generating and displaying the test value representation having a test value representation width measured in the second direction that is greater than a test parameter indicator width, of the first test parameter indicator, measured in the first direction.

18. The computerized method of claim 16, wherein in response to the test value exceeding the lower test parameter threshold, generating and displaying the test value representation having a test value representation width measured in the second direction that is greater than a test parameter indicator width, of the first test parameter indicator, as measured in the first direction.

19. The computerized method of claim 16, wherein the GUI further comprises a numerical value associated with the test value adjacent to the first test parameter indicator, and wherein the method further comprises:

modifying a first scale of the timeline to a second scale of the timeline based on a compressing input, the second scale of the timeline comprising a greater timespan than the first scale; and removing the numerical value associated with the test value from the GUI.

20. The computerized method of claim 16, further comprising modifying a first length of the test value representation to a second length of the test value representation based on a compressing input, the second length being less than the first length, and the first length and the second length being measured in the first direction.

* * * * *